United States Patent
Berg (12)

(10) Patent No.: US 6,210,670 B1
(45) Date of Patent: *Apr. 3, 2001

(54) CROSS-REACTING MONOCLONAL ANTIBODIES SPECIFIC FOR E-SELECTIN AND P-SELECTIN

(75) Inventor: Ellen L. Berg, Palo Alto, CA (US)

(73) Assignee: Protein Design Labs, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/619,491

(22) PCT Filed: Jun. 7, 1995

(86) PCT No.: PCT/US95/07302

§ 371 Date: Mar. 26, 1996

§ 102(e) Date: Mar. 26, 1996

(87) PCT Pub. No.: WO95/34324

PCT Pub. Date: Dec. 21, 1995

Related U.S. Application Data

(63) Continuation-in-part of application No. 08/259,963, filed on Jun. 14, 1994, now Pat. No. 5,622,701.

(51) Int. Cl.[7] .................... A61K 39/395; C07K 16/28; C12N 15/13; C12N 5/12

(52) U.S. Cl. .................... 424/153.1; 424/133.1; 424/141.1; 424/143.1; 424/173.1; 435/70.21; 435/69.6; 435/452; 435/455; 435/328; 435/343; 435/346; 435/465; 530/388.1; 530/387.3; 530/388.22; 530/388.7; 530/23.1; 530/23.5; 530/23.53

(58) Field of Search .................... 424/130.1, 133.1, 424/135.1, 143.1, 144.1, 139.1, 152.1, 141.1, 153.1, 172.1, 173.1; 435/7.1, 7.2, 7.21, 7.24, 70.21, 69.6, 69.1, 71.1, 172.2, 172.3, 320.1, 325, 326, 328, 331, 332, 334, 373, 343.1, 346, 440, 455, 465, 466, 471, 475, 476, 451, 452; 530/387.1, 387.3, 387.9, 388.1, 388.2, 388.22, 388.7, 388.73; 536/23.1, 23.5, 23.53

(56) References Cited

U.S. PATENT DOCUMENTS

| 5,225,539 | 7/1993 | Winter . |
| 5,378,464 | * 1/1995 | McEver . |
| 5,530,101 | * 6/1996 | Queen et al. . |
| 5,622,701 | * 4/1997 | Berg . |
| 5,632,991 | * 5/1997 | Gimbrone . |

FOREIGN PATENT DOCUMENTS

| WO 90/07861 | 7/1990 | (WO) . |
| WO 93/24614 | 12/1993 | (WO) . |

OTHER PUBLICATIONS

Kahan Curr. Opinion Immunology 4:553–560 (1992).*
Albelds et al. Fasteb J. 8: 504–512 (1994).*
Sdgington Biotechnology 10: 383–389 (1992).*
Larsen et al. J. Bioc. Chem. 267: 11104–11110 (1992).*
Ward et al. Therapeuric Immunology 1: 165–171 (1994).*
Natanson et al. Ann Int Med 120: 771–783 (1994).*
Carroway et al. Am. J. Resp. Crit. Care Med. 157 (3 Part 1): 938–949.*
Mulligan et al. J Clin Invest. 90: 1600–1607 (1992).*
Larsen, G.R. et al.; "P–selectin and E–selectin, distinct but overlapping leukocyte ligand specificities"; J. Biol. Chem., vol. 267, No. 16, Jun. 5, 1992, pp. 11104–11110.
Picker, L.J. et al.; "The neutrophil selectin LECAM–1 presents carbohydrate ligands . . . GMP–140"; Cell, vol. 66, Sep. 6, 1991, pp. 921–933.
Kearney, John F. (1984) *Fundamental Immunology* 751–766. Hyberidomas and Monoclonal Antibodies.
Goding, James W. (1986) Monoclonal Antibodies: Principles and Practice Ch. 3, Academic Press. pp. 86–103.
J. McDougal et al. (1988) *J. Immunology* 137:2937–2944. Binding of the Human Retrovirus HTLV–III/LAV/ARV/HIV to the CD4 (T4).
Abbassi et al. (1991) *J. Immunology* 147:2107–2115. Canine neutrophil margination mediated by lectin adhesion molecule–1 in vitro.
E. Berg et al. (1992) *Biochem. Biophys. Res. Comm.* 184:1048–1055 Comparison of L–Selectin and E–Selectin Ligand Specificities.
Cunningham et al. (1992) *Tibtech* vol. 10: 112–113 Antibodies engineering –how to be human.
Jutila et al. (1992) *J. Exp. Med.* 175:1565–1573. Characterization of a functionally important and evolutionarily well–conserved epitope mapped to the short consensus repeats of E–selectin and L–selectin.
"Antibodies" excerpt, R&D Systems 1993 Catalog, Minneapolis, MN.
"Adhesion Molecule Antibodies" R&D Systems 1994 Catalog, Minneapolis, MN.
D. Erbe et al. (1993) *J. Cell Biology* 120:1227–1235. p–to and E–Selectin Use Common Sites for Carbohydrate Ligand Recognition and Cell Adhesion.
A. Gearing et al. (1993) *Immunology Today* 14:506–512. Circulating adhesion molecules in disease.
S. Emery et al. (1994) *Exp. Opin. Invest. Drugs* 3:241–251. Humanised monoclonal antibodies for therapeutic applications.
A. Seekamp et al. (1994) *Am. J. of Pathology* 144:592–598. Role of Selectins in Local and Remote Tissue Injury following Ischemia and Reperfusion.
Berg et al. (1995) *Blood* 85:31–37.

* cited by examiner

*Primary Examiner*—Phillip Gambel
(74) *Attorney, Agent, or Firm*—Townsend & Townsend & Crew LLP; John Storella

(57) ABSTRACT

This invention provides monoclonal antibodies that bind to both E-selectin and to P-selectin, and inhibit the binding of these proteins to counterreceptors. The invention also provides nucleic acids encoding these antibodies and methods for using the antibodies in the treatment of inflammatory conditions.

55 Claims, 14 Drawing Sheets

```
ATG GAT TTT CAA GTG CAG ATT TTC AGC TTC CTG CTA ATC AGT GCC TCA GTC ATA ATA TCC     60
 M   D   F   Q   V   Q   I   F   S   F   L   L   I   S   A   S   V   I   I   S

AGA GGA CAA ATT GTT CTC ACC CAG TCT CCA GCA ATC ATG TCT CCA TCT GCA TCT CCA GGG GAG AAG    120
 R   G   Q   I   V   L   T   Q   S   P   A   I   M   S   P   S   A   S   P   G   E   K

GTC ACC ATG ACC TGC AGT GCC AGC TCA AGT GTG CCT TAC ATG CAC TGG TAT CAG CAG AAG    180
 V   T   M   T   C   S   A   S   S   S   V   P   Y   M   H   W   Y   Q   Q   K

TCA GGC ACC TCC CCC AAA TTA TGG ATT TAT GAC ACA TCC AAT CTG GCT TCT GGA GTC CCT    240
 S   G   T   S   P   K   L   W   I   Y   D   T   S   N   L   A   S   G   V   P

GCT CGC TTC AGT GGC AGT GGG TCT GGG ACC TCT TAC TCT CTC ACA ATC AGC AGC ATG GAG    300
 A   R   F   S   G   S   G   S   G   T   S   Y   S   L   T   I   S   S   M   E

GCT GAA GAT GCT GCC ACT TAT TAC TGC CAG CAG TGG AGT AGT GAC CCA TTC ACG TTC GGC    360
 A   E   D   A   A   T   Y   Y   C   Q   Q   W   S   S   D   P   F   T   F   G

TCG GGG ACA AAG TTG GAA ATA AAG
 S   G   T   K   L   E   I   K
```

FIG. 7A.

```
ATG GAC TCC AGG CTC AAT TTA GTT TTC CTT GTC CTT ATT TTA AAA GGT GTC CAG TGT GAT    60
 M   D   S   R   L   N   L   V   F   L   V   L   I   L   K   G   V   Q   C   D

GTA CGA CTG GTG GAG TCT GGG GGA GGT TTA GTG CAG CCT GGA GGG TCC CGG AAA CTC TCC   120
 V   R   L   V   E   S   G   G   G   L   V   Q   P   G   G   S   R   K   L   S

TGT GCA GCC TCT GGA TTC ACT TTC AGT AGC TTT GGA ATG CAC TGG GTT CGT CAG GCT CCT   180
 C   A   A   S   G   F   T   F   S   S   F   G   M   H   W   V   R   Q   A   P

GAT AAG GGG CTG GAG TGG GTC GCA TTC ATT AGC AGT GGC AGT AGT ACC ATC TAC TAT GCT   240
 D   K   G   L   E   W   V   A   F   I   S   S   G   S   S   T   I   Y   Y   A

GAC ACA GTG AGG GGC CGA TTC ACC ATC TCC AGA GAC AGT CCC AAG AAC ACC CTG TTC CTG   300
 D   T   V   R   G   R   F   T   I   S   R   D   S   P   K   N   T   L   F   L

CAA ATG ACC AGT CTA AGG TCT GAG GAC ACG GCC ATG TAT TAC TGT GCA AGA CCT TTA CCC   360
 Q   M   T   S   L   R   S   E   D   T   A   M   Y   Y   C   A   R   P   L   P

CCG TTT GCT TAC TGG GGC CAA GGG ACT TTG GTC ACT GTC TCT GCA                        390
 P   F   A   Y   W   G   Q   G   T   L   V   T   V   S   A
```

FIG. 7B.

```
ATG GAT TTT CAA GTG CAG ATT TTC AGC TTC CTG CTA ATC AGT GCC TCA GTC ATA ATA TCC
 M   D   F   Q   V   Q   I   F   S   F   L   L   I   S   A   S   V   I   I   S
                                  30                                          60

AGA GGA GAT ATT CAA ATG ACC CAG ACT CCA TCT AGC TTA TCT GCA TCT GTA GGG GAT AGG
 R   G   D   I   Q   M   T   Q   T   P   S   S   L   S   A   S   V   G   D   R
                                  90                                         120

GTC ACC ATA ACC TGC AGT GCC AGC TCA AGT GTG CCT TAC ATG CAC TGG TAT CAG CAG AAG
 V   T   I   T   C   S   A   S   S   S   V   P   Y   M   H   W   Y   Q   Q   K
                                 150                                         180

CCA GGC AAA GCC CCC AAA TTA TTG ATT TAT GAC ACA TCC AAT CTG GCT TCT GGG GTA CCT
 P   G   K   A   P   K   L   L   I   Y   D   T   S   N   L   A   S   G   V   P
                                 210                                         240

TCT CGC TTC AGT GGC AGT GGG TCT GGG ACC TCT TAC ACT CTC ACA ATC AGC AGC CTG CAG
 S   R   F   S   G   S   G   S   G   T   S   Y   T   L   T   I   S   S   L   Q
                                 270                                         300

CCT GAA GAT TTT GCC ACT TAT TAC TGC CAG CAG TGG AGT AGT GAC CCA TTC ACG TTC GGC
 P   E   D   F   A   T   Y   Y   C   Q   Q   W   S   S   D   P   F   T   F   G
                                 330                                         360

CAG GGG ACA AAG GTG GAA ATA AAA
 Q   G   T   K   V   E   I   K
```

FIG. 8A.

```
ATG GAC TCC AGG CTC AAT TTA GTT TTC CTT GTC CTT ATT TTA AAA GGT GTC CAG TGT GAA    60
 M   D   S   R   L   N   L   V   F   L   V   L   I   L   K   G   V   Q   C   E
                                    30                                              E
GTG CAA CTG GTG GAG TCT GGG GGA GGT TTA GTG CAG CCT GGA GGG TCC CTT CGT CTC TCC   120
 V   Q   L   V   E   S   G   G   G   L   V   Q   P   G   G   S   L   R   L   S
                                    90
TGT GCA GCC TCT GGA TTC ACT TTC AGT AGC TTT GGA ATG CAC TGG GTT CGT CAG GCT CCT   180
 C   A   A   S   G   F   T   F   S   S   F   G   M   H   W   V   R   Q   A   P
                                   150
GGT AAG GGG CTG GAG TGG GTC GCA TTC ATT AGT AGT GGC AGT TCG ACC ATC TAC TAT GCT   240
 G   K   G   L   E   W   V   A   F   I   S   S   G   S   S   T   I   Y   Y   A
                                   210
GAC ACA GTG AGG GGC CGA TTC ACC ATC TCC AGA GAC AAT TCT AAG AAC ACC CTG TAT CTG   300
 D   T   V   R   G   R   F   T   I   S   R   D   N   S   K   N   T   L   Y   L
                                   270
CAA ATG AAC AGT CTA AGG GCT GAG GAC ACG GCC GTG TAT TAC TGT GCA AGA CCT TTA CCC   360
 Q   M   N   S   L   R   A   E   D   T   A   V   Y   Y   C   A   R   P   L   P
                                   330
CCG TTT GCT TAC TGG GGC CAA GGG ACT TTG GTC ACT GTC TCT GCA
 P   F   A   Y   W   G   Q   G   T   L   V   T   V   S   A
                                   390
```

FIG. 8B.

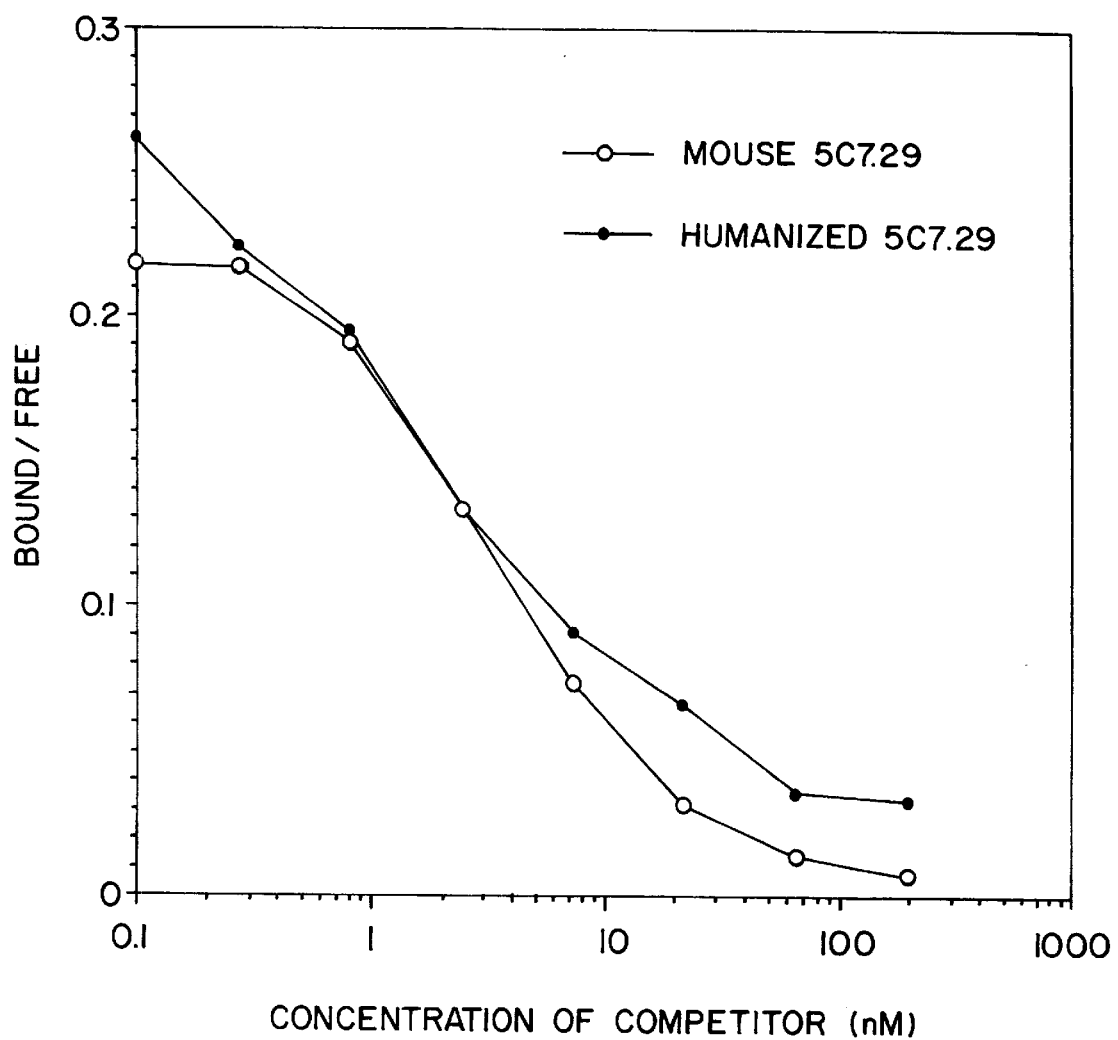
FIG. IIA.

CROSS-REACTING MONOCLONAL ANTIBODIES SPECIFIC FOR E-SELECTIN AND P-SELECTIN

This application is the United States national stage of PCT/US95/07302, filed Jun. 7, 1995, which is a continuation-in-part of application Ser. No. 08/259,963, filed Jun. 14, 1994, now U.S. Pat. No. 5,622,701.

BACKGROUND OF THE INVENTION

The ability of cells to adhere to one another plays a critical role in development, normal physiology, and disease processes such as inflammation. This ability is mediated by adhesion molecules, generally glycoproteins, expressed on cell membranes. Often, an adhesion molecule on one cell type will bind to another adhesion molecule expressed on a different cell type, forming a receptor counter-receptor pair. Three important classes of adhesion molecules are the integrins, selecting, and immunoglobulin (Ig) superfamily members (see Springer, Nature 346:425 (1990); Osborn, Cell 62:3 (1990); Hynes, Cell 69:11 (1992). These molecules are vital to the interaction of leukocytes and platelets with themselves and with the extracellular matrix and vascular endothelium.

The selectin family of receptors are so named because of their lectin-like domain and the selective nature of their adhesive functions. There are three known selecting, L-selectin (also known as LECAM-1, Mel-14 or LAM-1 or CD62L), E-selectin (also called ELAM-1 or CD62E) and P-selectin (also known as CD62, CD62P, GMP140 or PADGEM). The selecting are highly homologous, containing a 120 amino acid (aa) N-terminal lectin domain, an EGF-like domain, a variable number of multiple short consensus repeat (SCR) domains homologous to those found in complement regulatory proteins, followed by a transmembrane domain and short cytoplasmic tail. See Siegelman et al., Science 243:1165–1172 (1989); Lasky et al., Cell 56:1045–1055 (1989); Tedder et al., J. Exp. Med. 170:123–133 (1989); Johnson et al., Cell 56:1033–1044 (1989); Bevilacqua et al., Proc. Natl. Acad. Sci. USA 84:9238–9242 (1987), Bevilacqua et al., Science 243:1160–1165 (1989), Bevilacqua et al., J. Clin. Invest. 91:379–387 (1993), Camerini et al., Nature 280:496–498 (1989). The selecting have overlapping but distinct specificities for counterreceptors. See Bevilacqua et al., J. Clin. Invest. 91:379–387 (1993); Feize, Current Opinion in Struct. Biol. 3:701–710 (1993); Berg et al., Biochem. Biophys. Res. Comm. 184:1048–1055 (1992); Foxall et al., J. Cell Biol. 117:895–902 (1992); Larsen et al., J. Biol. Chem. 267:11104–11110 (1992); Polley et al., Proc. Natl. Acad. Sci. USA 88:6224–6228 (1991) (each of which is incorporated by reference in its entirety for all purposes).

P-selectin is constitutively expressed by both platelets and endothelial cells where it is stored in α-granules or Weibel-Palade bodies for rapid (seconds to minutes) translocation to the cell surface upon activation by, for example, thrombin or histamine (McEver et al., J. Biol. Chem. 250:9799–9804 (1984); Hsu-Lin et al., J. Biol. Chem. 264:8121–9126 (1984)). E-selectin is expressed by activated endothelial cells (e.g., after TNF-α or IL-1 stimulation for 6–8 hr). Its expression is controlled at the transcriptional level (Bevilacqua et al., 1987, supra; Bevilacqua et al., 1989, supra). P-selectin and E-selectin both bind to neutrophils and monocytes (Larsen et al., Cell 59:305–312 (1989); Johnston et al., Cell 56:1033–1044 (1989); Bevilacqua et al., 1987, supra; Bevilacqua et al., 1989, supra), as well as subsets of lymphocytes (Picker et al., Nature 349:796–799 (1991); Shimizu et al., Nature 349:799–802 (1991); Moore et al., BBRC 186:173–181 (1992)). L-selectin is constitutively expressed by leukocytes, and mediates lymphocyte adhesion to peripheral lymph node high endothelial venules (HEV) (Gallatin et al., Nature 304:30–34 (1983); Berg et al., Immunol. Rev. 108:5–18 (1989); Berg et al., J. Cell. Biol. 114:343–349 (1991)), and neutrophil adhesion to cytokine-activated endothelial cells (Hallman et al., Biochem. Biophys. Res. Comm. 174:236–243 (1991); Smith et al., J. Clin. Invest. 87:609–618 (1991); Spertini et al., J. Immunol. 147:2565–2573 (1991)). L-selectin is a counter-receptor on neutrophils for both E-selectin and P-selectin (Kishimoto et al., Blood 78:805–811 (1990), Picker et al., Cell 66:921 (1991)), although all three selectins probably have other counter-receptors as well.

E-selectin, P-selectin and L-selectin mediate leukocyte-endothelial cell and platelet-leukocyte adhesive interactions during inflammation (Bevilacqua et al., 1993, supra). All three selectins have been demonstrated to participate in an initial "rolling" interaction of leukocytes with activated endothelium (von Andrian et al., Proc. Natl. Acad. Sci. USA 88:7538–7542 (1991); Ley et al., Blood 77:2553–2555 (1991); Abassi et al., J. Clin. Invest. 92:2719–2730 (1993); Dore et al., Blood 82:1308–1316 (1993); Jones et al., Biophys. J. 65:1560–1569 (1993); Mayadas et al., Cell 74:541–554 (1993)). This initial interaction precedes CD18-integrin-mediated adhesion and subsequent migration of neutrophils through the endothelium and into inflamed tissue sites (Lawrence et al., Cell 65:859–873 (1991); von Andrian et al., Am. J. Physiol. 263:H1034–H1044 (1992)). Depending on the nature of inflammatory stimuli and time after initiation of inflammatory response, either E-selectin or P-selectin may be functionally dominant in promoting neutrophil-mediated tissue damage.

In principle, antibodies or other antagonists of the selecting could abort the adhesion process, thereby preventing neutrophils from binding to the endothelium and from extravasating into tissues. A substantial number of antibodies specific for one of the selecting have been reported. Some of these antibodies have been reported to block binding of selecting to counterreceptors in vitro. Some of the antibodies have also been reported to block selectin-mediated interactions in animal models in vivo. For example, antibodies to E-selectin have been reported to protect against neutrophil-mediated damage in an IgG complex model of lung injury in the rat (Mulligan et al., J. Clin. Invest. 88:1396 (1991)). Antibodies to P-selectin have been reported to protect against acute lung injury induced by intravenous injection of cobra venom factor (Mulligan et al., J. Clin. Invest. 90:1600–1607 (1992)), as well as in a rat model of systemic endotoxemia (Coughlan et al., J. Exp. Med. 179:329–334 (1994)). Antibodies to P-selectin have also been reported to be protective in a cat model of myocardial ischemia and reperfusion injury (Weyrich et al., FASEB J. 7:A785 (1993)).

Although some antibodies against E-selectin and P-selectin have shown blocking activity, many, if not most, antibodies specific for E-selectin or P-selectin are nonblocking (see, e.g., Bevilacqua et al., 1989, supra; Erbe et al., J. Cell Biol. 119:215–227 (1992)). That is, these antibodies bind to epitopes in the extracellular domains of E-selectin or P-selectin that do not directly participate in counterreceptor binding or the subsequent cellular adhesion process. The prevalence of nonblocking antibodies suggests that only small regions of the extracellular domain participate directly in binding or influence binding. Thus, de novo screening of antibodies generated against E-selectin or P-selectin would be expected to generate mainly nonblocking antibodies.

Despite the large number of antibodies isolated to-date against the three selectins, there have been few reports of crossreacting antibodies that bind to more than one selectin. Crossreacting antibodies might be capable of aborting the inflammatory process at more than one level, thereby providing more broadly useful therapeutic agents for neutrophil-mediated inflammatory conditions than antibodies specific for a single selectin. One antibody has been reported to crossreact with human E-selectin and dog L-selectin but not with the two selectins from the same species (Abassi et al., *J. Immunol.* 147:2107–2115 (1991)). A second antibody has been reported to crossreact with human E-selectin and L-selectins (Jutila et al., *J. Exp. Med.* 175:1565–1573 (1992); WO/9324614). However, no antibody has been isolated that binds to both P-selectin and E-selectin, much less blocks the functions of both of these molecules.

Accordingly, there is a need for antibodies that bind to both E-selectin and P-selectin, preferably so as to block the capacity of both of these molecules to participate in adhesion reactions with counterreceptors. The present invention fulfills this and other needs.

SUMMARY OF THE INVENTION

The invention provides monoclonal antibodies that have a binding site that specifically binds to P-selectin and to E-selectin. For many such antibodies, specific binding of the antibody to the P-selectin inhibits binding of the P-selectin to a counterreceptor of P-selectin, and specific binding of the antibody to E-selectin inhibits binding of the E-selectin to a counterreceptor of E-selectin. Counterreceptors of E-selectin and P-selectin are expressed on the surface of cells such as HL-60 cells and neutrophils. Exemplary antibodies are designated 57C.29, 2C9.11 and 1D8.10. Many of the antibodies of the invention compete with an exemplified antibody for specific binding to P-selectin and to E-selectin. Some antibodies of the invention also specifically bind to L-selectin, whereas others do not. In one embodiment the antibody recognizes an epitope of E-selectin comprising amino acids $Q_{21}$, $R_{22}$, $Y_{23}$, $T_{119}$, and $A_{120}$. In another embodiment, the antibodies bind to the same epitope of E-selectin and/or P-selectin as antibody 5C7.29. In addition to intact antibodies, the invention also provides binding fragments such as Fab, Fab', F(ab')$_2$, Fv or single-chain antibodies.

Some of the antibodies of the invention are non-human, e.g., mouse, whereas others are humanized or human antibodies. A humanized antibody comprises a humanized heavy chain variable region and a humanized light chain variable region. The humanized light chain variable region can comprise complementarity determining regions (e.g., CDR1, CDR2, CDR3) having amino acid sequences from the light chain of a mouse, antibody selected from the group consisting of 5C7.29, 2C9.11 and 1D8.10, and having a variable region framework sequence substantially identical to a human light chain variable region framework sequence. The humanized heavy chain variable region can comprise complementarity determining regions (e.g., CDR1, CDR2 and CDR3) having amino acid sequences from the corresponding mouse antibody heavy chain, and having a variable region framework sequence substantially identical to a human heavy chain variable region framework sequence. The antibodies optionally contain constant regions substantially identical to human constant regions.

In particular embodiments of the humanized antibodies of this invention, the humanized light chain variable region has a sequence substantially identical to the mature sequence depicted in FIG. 8A [SEQ ID NO:6] and the humanized heavy chain variable region has a sequence substantially identical to the mature sequences depicted in FIG. 8B [SEQ ID NO:8]. More particularly, this invention provides humanized antibodies wherein (a) the humanized light chain variable region has the sequence: $X_1IX_2X_3$TQSPSS LSAS-VGDRVT ITCSASSS$X_{11}$P Y$X_{12}$HWYQQKPG KAPKLLIYDT SN$X_{13}X_{14}X_{15}$GVPX$_4$R X$_7$SGSGSGTX$_5$X$_6$ TX$_8$TISSLQPE DX$_9$ATYYCX$_{16}X_{17}$W SSDPFTFGX$_{10}$G TKVEIK [SEQ ID NO:9], wherein X$_1$=D or Q; X$_2$=Q or V; X$_3$=M or L; X$_4$=S or A; X$_5$=S or D; X$_6$=Y or F; X$_7$=F or I; X$_8$=L or F; X$_9$=F, I or A; X$_{10}$=Q, G or S; X$_{11}$=V, I or L; X$_{12}$=M or L; X$_{13}$=any amino acid; X$_{14}$=any amino acid; X$_{15}$=S or T; X$_{16}$=Q, N or H; and X$_{17}$=Q, N or H; and (b) the humanized heavy chain variable region has the sequence: X$_3$VQLVESGGG LVQPGGSLRL SCAASG-FTFS SFGX$_7$HWVRQA PGKGLEWVX$_1$F ISSGSSTIYY X$_8$X$_9$X$_{10}$X$_{11}$X$_{12}$X$_{13}$RFTI SRDNX$_4$KNX$_5$LY LQMX$_2$SLRAED TAVYYCARPL PPFAYWGQGT LVTVSX$_6$ [SEQ ID NO:10]; wherein, X$_1$=A or S; X$_2$=N or T; X$_3$=E, Q or D; X$_4$=S, A or P; X$_5$=T or S; X$_6$=A or S; X$_7$=M, I, V or L; X$_8$=any amino acid; X$_9$=any amino acid; X$_{10}$=any amino acid; X$_{11}$=V, A, I, L, M or F; X$_{12}$=R, K or Q; and X$_{13}$=G, A, D, T or S. In certain embodiments of the aforementioned antibodies, the CDR regions of the light and heavy chain variable regions have the same amino acid sequence as the CDR sequences of FIGS. 8A and 8B. That is, in the human light chain variable region, X$_{11}$=V; X$_{12}$=M; X$_{13}$=L; X$_{14}$=A; X$_{15}$=S; X$_{16}$=Q; and X$_{17}$=Q; and in the heavy chain variable region, X$_7$=M; X$_8$=A; X$_9$=D; X$_{10}$=T; X$_{11}$=V; X$_{12}$=R; and X$_{13}$=G. In another embodiment, the variable light and heavy chain regions have the amino acid sequence depicted in FIGS. 8A and 8B.

In another aspect, the invention provides purified nucleic acid segments encoding a light or heavy chain variable region of one of the monoclonal antibodies discussed above.

The invention also provides stable cell lines capable of producing the antibodies described above. The stable cell lines comprise nucleic acid segments respectively encoding the heavy chain and light chain of an antibody described above. The segments are operably linked to first and second promoters to allow expression of the heavy and light chains.

The invention further provides pharmaceutical compositions comprising the antibodies described above and methods of treatment using the same. The methods of treatment are particularly effective for inflammatory diseases including conditions such as ischemia-reperfusion injury, adult respiratory distress syndrome, sepsis, psoriasis and autoimmune disease.

In another aspect, the invention provides methods of generating an antibody capable of blocking E-selectin and/or P-selectin mediated functions. The method comprises concurrently or consecutively immunizing a mammal with P-selectin and E-selectin. B-cells from the mammal are immortalized to generate immortalized cells producing antibodies. An immortalized cell is selected producing an antibody that specifically binds to E-selectin and to P-selectin.

The invention further provides methods of detecting E-selectin and P-selectin bearing cells in a biological sample suspected of containing the cells. The method comprises contacting the sample with an antibody as described above to form an immune complex with the E-selectin and/or P-selectin bearing cells. The presence of the immune complex is then detected to indicate the presence of the cells.

BRIEF DESCRIPTION OF THE DRAWINGS

FIGS. 7A–7B. Sequences of the CDNA (light chain—SEQ ID NO:1; heavy chain—SEQ ID NO:3) and translated amino acid sequences (light chain—SEQ ID NO:2; heavy chain—SEQ ID NO:4) of the light chain (A) and heavy chain (B) variable regions of the mouse 5C7.29 antibody. The first amino acid of each mature chain is indicated by a double underline. The three CDRs in each chain are underlined.

FIGS. 8A–8B. Sequences of the synthetic DNA (light chain—SEQ ID NO.:5; heavy chain—SEQ ID NO:7) and translated amino acid sequences (light chain—SEQ ID NO:6; heavy chain—SEQ ID NO:8) of the light chain (A) and heavy chain (B) variable regions of the humanized 5C7.29 antibody. The first amino acid of each mature chain is indicated by a double underline. The three CDRs in each chain are underlined.

FIGS. 11A and 11B. Competitive binding of mouse and humanized 5C7.29 antibodies to cells expressing E-selectin (A) or P-selectin (B). Increasing concentrations of cold competitor antibody were incubated with the cells in the presence of radiolabeled tracer mouse 5C7.29 antibody, and the ratio of bound/free radioactivity was determined.

DEFINITIONS

Figure 1A:
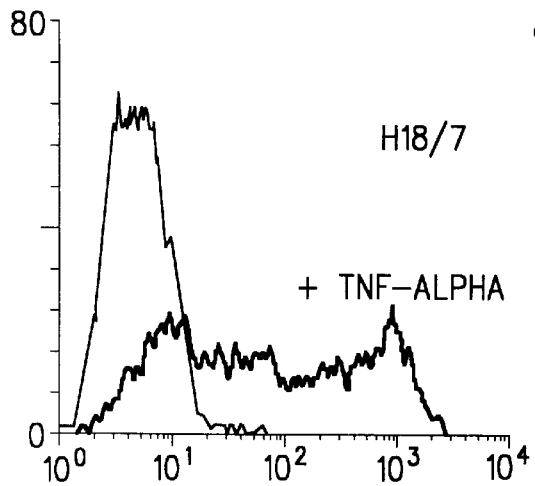
FIGS. 1A and 1B: Crossreacting antibody 5C7.29 binds to naturally occurring human E-selectin. (a) Binding of known anti-E-selectin antibody H18/7 to activated (black histograms) and resting (grey histograms) HUVEC cells. (b) Binding of crossreacting antibody 5C7.29 to activated and resting HUVEC cells. FACS fluorescence intensity is indicated by the X axis.

The term "substantial identity" or "substantial homology" means that two peptide sequences, when optimally aligned, such as by the programs GAP or BESTFIT using default gap weights, share at least 80 percent sequence identity, preferably 90 percent sequence identity, more preferably at least 95 percent sequence identity or more (e.g., 99 percent sequence identity). Preferably, residue positions which are not identical differ by conservative amino acid substitutions.

The term "substantially pure" or "isolated" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition. Most preferably, the object species is purified to essential homogeneity (contaminant species cannot be detected in the composition by conventional detection methods) wherein the composition consists essentially of a single macromolecular species.

"Immunoglobulin," "antibody" or "antibody peptide(s)" refers to an intact antibody, or a binding fragment thereof that competes with the intact antibody for specific binding. Binding fragments are produced by recombinant DNA techniques, or by enzymatic or chemical cleavage of intact immunoglobulins. Binding fragments include Fab, Fab', F(ab')$_2$, Fv and single-chain antibodies. An antibody other than a "bispecific" or "bifunctional" antibody is understood to have each of its binding sites identical.

An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term epitope includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

An antibody is said to specifically bind an antigen when the dissociation constant is $\leq 1$ μM, preferably $\leq 100$ nM and most preferably $\leq 10$ nM.

The term patient includes human and veterinary subjects.

The term P-selectin counterreceptor denotes a protein other than an antibody that specifically binds to P-selectin at least in part by noncovalent bonds. Specific binding maintains cells respectively bearing receptor and counterreceptor in physical proximity and may also transduce a change in physical or functional phenotype in either of the cells or both. Other selectin counterreceptors are analogously defined.

DESCRIPTION OF THE PREFERRED EMBODIMENT

I. Antibodies of the Invention

The invention provides antibodies that crossreact, i.e., specifically bind, with E-selectin and P-selectin. Preferred antibodies block the functions of both of these molecules.

A. General Characteristics of Antibodies

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, *J. Mol. Biol.* 196:901–917 (1987); Chothia et al., *Nature* 342:878–883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315–321 (1990); Kostelny et al., *J. Immunol.* 148, 1547–1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab' and Fv).

B. Binding Specificity and Affinity

The immunoglobulins (or antibodies) of the invention exhibit specific binding to both P-selectin and E-selectin. That is, a single binding site on an antibody has affinity for both P-selectin and E-selectin. Thus, the antibodies bind to epitopes that are common to both molecules. The antibodies bind to the natural and/or recombinant human forms for P-selectin and E-selectin (see Johnston et al., 1989, supra; Bevilacqua et al., 1989, supra). Some antibodies may also bind P-selectin and/or E-selectin from nonhuman species. Some of the antibodies also specifically bind to L-selectin (preferably human L-selectin (see Tedder, EPA 386,906 (1990)) whereas other antibodies of the invention do not. Surprisingly, the common epitopes bound by the crossreacting antibodies of the invention are also epitopes important for both E-selectin and P-selectin to interact with their counterreceptors on activated leukocytes, such as neutrophils. Thus, most crossreacting antibodies of the invention block the functional interactions of E-selectin or P-selectin and usually those of both of these molecules. Some crossreacting antibodies also block the functional interactions of L-selectin whereas others do not.

Blockage of P-selectin-mediated functions can be demonstrated in vitro. In vitro assays measure the capacity of an antibody to inhibit binding of P-selectin to a counterreceptor. Suitable sources of P-selectin for such assays are purified P-selectin (or an extracellular domain thereof), cells transfected with P-selectin, activated endothelial cells or platelets. Suitable sources of counterreceptor are leukocytes, neutrophils, monocytes, or HL-60 cells (ATCC CCL 240) and appropriate cell lines transfected with L-selectin. Neutrophils can be isolated from whole blood (preferably human blood) by Ficoll-Hypaque gradient centrifugation. Neutrophils are usually pretreated with rabbit serum to block Fc receptors before adding to a binding assay. When both components in the binding assay are cellular, binding can be assayed microscopically or by flow cytometry. See Kishimoto et al., supra. When one or both components is a purified protein, one component is usually immobilized to a solid phase and the other labelled. Binding is then assayed from label bound to the solid phase. Usually, the antibody is preincubated with the source of P-selectin before adding the source of counterreceptor to the incubation mixture. Blocking activity is shown when an excess of antibody, i.e., 5-fold, 10-fold or up to 100-fold, substantially inhibits binding of P-selectin to its counterreceptor. The precise degree of inhibition will depend on the assay used. In an assay that measures inhibition of platelet binding to HL-60 cells, an excess of P-selectin blocking antibodies typically exhibits at least 50, 60, 70, 80 or 90% and usually about 80–90% inhibition.

The binding specificity of many blocking antibodies of the invention is further defined by their capacity to bind P-selectin in the complete or substantial absence of $Ca^{++}$ (e.g., in the presence of 2 mM EDTA (a calcium chelator) and the absence of $Ca^{++}$ in an in vitro assay). By contrast, most blocking antibodies against P-selectin isolated to date require $Ca^{++}$ for activity. See Geng et al., *J. Biol. Chem.* 266:22313–22318 (1991). Antibodies requiring a $Ca^{++}$ cofactor for blocking activity may be less effective in in vivo conditions where levels of $Ca^{++}$ are expected to fluctuate.

The capacity of the antibodies of the invention to block E-selectin-mediated functions can be demonstrated by analogous in vitro assays to those employed to show blocking of P-selectin mediated functions. Suitable sources of E-selectin are mammalian cell lines transfected with E-selectin, activated endothelial cells, as well as purified E-selectin (or extracellular domains thereof). If the assay is performed using purified E-selectin, the E-selectin can be immobilized to a solid support. Suitable sources of counterreceptors to E-selectin are leukocytes, neutrophils, monocytes, and HL-60 cells and appropriate cell lines transfected with L-selectin. The degree of binding inhibition will again depend on the components in the assay. In an assay that measures binding between activated endothelial cells and HL-60 cells, the antibodies of the invention, when present in excess, typically exhibit at least about 20, 40, 60, 80% inhibition or more typically about 25–75% or 50% inhibition.

The capacity of antibodies to block L-selectin mediated functions can be demonstrated in a variety of in vitro assays. See, e.g., copending application Ser. No. 08/160,516, filed Nov. 30, 1993 and Ser. No. 08/160,074, filed Nov. 30, 1993 (incorporated by reference in their entirety for all purposes). A simple visual assay for detecting such interaction has been described by Kishimoto et al., supra. Briefly, monolayers of human umbilical vein cells are stimulated with IL-1. Neutrophils, with or without pretreatment with the antibody under test, are added to the monolayer under defined conditions, and the number of adhering neutrophils is determined microscopically. In one method, the neutrophils are obtained from human leukocyte adhesion deficient patients. See Anderson et al., Ann. Rev. Med. 38:175 (1987). The neutrophils from such patients lack integrin receptors, whose binding to neutrophils might obscure the effects of blocking L-selectin binding.

Preferred antibodies selectively bind a functional epitope on P-selectin and E-selectin molecules associated with a response to tissue injury and inflammation. Binding of the antibodies to a functional epitope on P-selectin and E-selectin effectively inhibits adhesion of leukocytes to the activated vascular endothelium and/or to activated platelets in vivo. Preferred antibodies impair the adhesion of leukocytes to the activated vascular endothelium to prevent or inhibit an inflammatory and/or thrombotic condition.

In vivo blocking efficacy can be demonstrated in the same animal models that have been used to show efficacy for antibodies specific for a single adhesion molecule. For example, Mulligan et al., 1991, 1992, supra, describe rat models to test the efficacy of antibodies in protecting against lung injury; Coughlan et al., 1994, describe a rat model for testing the efficacy of antibodies in treatment of systemic endotoxemia; and Weyrich et al., supra, describe a cat model for testing the protective effect of antibodies in myocardial ischemia and reperfusion injury. Other animal models for various inflammatory diseases and disorders are described by Arfors et al., Blood 69:338 (1987) (skin lesions); Tuomanen et al., J. Exp. Med. 170:959 (1989) (brain edema and death produced by bacterial meningitis); Lindbom et al., Clin. Immunol. Immunopath. 57:105 (1990) (tissue edema associated with delayed-type hypersensitivity reactions); Wegner et al., Science 247:456 (1990) (airway hyperresponsiveness in allergic asthma); Goldman et al., FASEB J. 5:A509 (1991) (remote lung injury following aspiration); Gundel et al., J. Clin. Invest. 88:1407 (1991) (late-phase bronchoconstriction following antigen challenge); Hutchings et al., Nature 346:639 (1990) (diabetes); Flavin et al., Transplant, Proc. 23:533 (1991) (cardiac allograft survival); Wegner et al., Am. Rev. Respir. Dis. 143:A544 (1991) (lung damage and dysfunction secondary to oxygen toxicity); Cosimi et al., J. Immunol. 144:4604 (1990) (renal allograft rejection); Jasin et al., Arthritis Rheum. 33:S34 (1990) (antigen-induced arthritis); Thomas et al., FASEB J. 5:A509 (1991) (vascular injury and death in endotoxic shock); Bucky et al., Proc. Am. Burn Assoc. 23:133 (1991) (burns); Hernandez et al., Am. J. Physiol. 253:H699 (1987) (permeability edema following ischemia reperfusion (IR) of intestine); Winquist et al., Circulation 82:III (1990); Ma et al., Cir. Res. 82:III (1990) (myocardial damage following myocardial infarction); Mileski et al., Surgery 108:206 (1990) (vascular and tissue damage following hemorrhagic shock and resuscitation); Clark et al., Stroke 22:877 (1991) (central nervous system damage following I/R of the spinal cord); Mileski et al., Proc. Am. Burn Assoc. 22:164 (1990) (edema and tissue damage following frostbite and rewarming); Simpson et al., Circulation 81:226 (1990) (infarct size following I/R of myocardium). Preferred antibodies show efficacy in at least one and usually several of these inflammatory and thrombotic diseases and conditions.

Many of the blocking antibodies of the invention show the same or similar binding specificity as one of the exemplary antibodies designated 5C7.29, 2C9.11 and 1D8.10. That is, the antibodies compete with at least one of the exemplified antibodies for specific binding to E-selectin and/or P-selectin. The E-selectin and P-selectin used in the test is preferably human, and may be natural or recombinant. Competition between antibodies is determined by an assay in which the immunoglobulin under test inhibits specific binding of a reference antibody (e.g., 5C7.29) to an antigenic determinant on a P-selectin and/or E-selectin molecule. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242–253 (1983)); solid phase direct biotin-avidin EIA (see Kirkland et al., J. Immunol. 137:3614–3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Molec. Immunol. 25(1):7–15 (1988)); solid phase direct biotin-avidin EIA (Cheung et al., Virology 176:546–552 (1990)); and direct labeled RIA (Moldenhauer et al., Scand. J. Immunol. 32:77–82 (1990)). Typically, such an assay involves the use of purified P-selectin or E-selectin bound to a solid surface or cells bearing either of these, an unlabelled test immunoglobulin and a labelled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to P-selectin and/or E-selectin by at least 50 or 75%.

The antibodies of the invention usually exhibit a specific binding affinity for P-selectin and E-selectin of greater than or equal to about $10^6$, $10^7$, $10^8$, $10^9$, or $10^{10}$ $M^{-1}$. However, antibodies do not necessarily show the same specific binding affinity for each of these ligands. Usually the upper limit of binding affinity of the antibodies is within a factor of about three, five or ten of that of one of the exemplified antibodies. Often the lower limit of binding affinity is also within a factor of about three, five or ten of that of the exemplified antibodies. The term "about" encompasses the degree of experimental error that may typically occur in the measurement of binding affinities.

A hybridoma producing the 5C7.29 antibody has been deposited with the American Type Culture Collection, 10801 University Boulevard, Manassas, Va. under the Budapest Treaty on May 25, 1994 and given the Accession No. ATCC CRL 11640. The production of this antibody is described in Example 1.

C. Production of Antibodies (1) Nonhuman Antibodies

Mouse, or other nonhuman antibodies crossreactive with P-selectin and E-selectin can be obtained using a variety of immunization strategies. In some strategies, nonhuman animals (usually nonhuman mammals), such as mice, are immunized with E-selectin and P-selectin antigens, either concurrently or consecutively. In other strategies, nonhuman animals are immunized with only one of these antigens. Preferred immunogens are cells stably transfected with P-selectin or E-selectin and expressing these molecules on their cell surface. Other preferred immunogens include P-selectin and E-selectin proteins or epitopic fragments of P-selectin and E-selectin containing the segments of these molecules that bind to the exemplified crossreacting antibodies.

Mouse or non-human antibodies crossreactive with all three selecting, i.e., P-selectin, E-selectin, and L-selectin, can be generated by similar strategies. Briefly, mice are immunized either simultaneously or sequentially with cells stably transfected with either P-selectin, E-selectin, or L-selectin, or purified selectin proteins or epitopic fragments thereof.

Antibody-producing cells obtained from the immunized animals are immortalized and selected for the production of an antibody which specifically binds to multiple selectins. See generally, Harlow & Lane, *Antibodies, A Laboratory Manual* (C.S.H.P. N.Y., 1988) (incorporated by reference for all purposes). The binding assays for the different selectins can be performed separately or concurrently. Concurrent analysis is conveniently performed by two-color FACS screening after incubation of hybridoma supernatants to cells transfected with selecting. For example, two populations of cells respectively expressing E-selectin and P-selectin are differentially labelled with a first label and tested for capacity to bind hybridomas supernatants. Binding is detected using an appropriate secondary antibody bearing a second label. This scheme is readily extendible to allow simultaneous detection of binding to all three selectins by differentially labelling three populations of cells respectively expressing E-selectin, P-selectin and L-selectin with different intensities of the first label. Alternatively, separate screening for E-selectin, P-selectin and, if desired, L-selectin binding, can be achieved by single color FACS analysis of supernatant binding to transfectant cells or by binding assay to immobilized E-selectin, P-selectin, or L-selectin. Crossreacting antibodies are then further screened for their capacity to block functional properties of E-selectin, P-selectin and L-selectin using the in vitro and in vivo assays described above. Most antibodies that crossreact with P-selectin or E-selectin also block the functional capacity of both of these molecules to interact with a counter-receptor.

(2) Humanized Antibodies

The invention provides humanized antibodies having similar binding specificity and affinity to selected mouse or other nonhuman antibodies. Humanized antibodies are formed by linking CDR regions (preferably CDR1, CDR2 and CDR3) of non-human antibodies to human framework and constant regions by recombinant DNA techniques. See Queen et al., *Proc. Natl. Acad. Sci. USA* 86:10029–10033 (1989) and WO 90/07861 (incorporated by reference in their entirety for all purposes). The humanized immunoglobulins have variable region framework residues substantially from a human immunoglobulin (termed an acceptor immunoglobulin) and complementarity determining regions substantially from a mouse immunoglobulin described above, e.g., the 5C7.29 antibody (referred to as the donor immunoglobulin). The constant region(s), if present, are also substantially from a human immunoglobulin.

In principal, a framework sequence from any human antibody may serve as the template for CDR grafting. However, it has been demonstrated that straight CDR replacement onto such a framework often leads to significant loss of binding affinity to the antigen (Glaser et al., *J. Immunol.* 149: 2606 (1992); Tempest et al., Biotechnology 9: 266 (1992); Shalaby et al., *J. Exp. Med.* 17: 217 (1992)). The more homologous a human antibody is to the original murine antibody, the less likely will combining the murine CDRs with the human framework be to introduce distortions into the CDRs that could reduce affinity. Therefore, homology (that is, percent sequence identity) of at least 65% between the humanized antibody variable region framework and the donor antibody variable region framework is preferred.

The heavy and light chain variable region framework residues can be derived from the same or different human antibody sequences. However, a heavy chain and light chain framework sequences chosen from the same human antibody reduce the possibility of incompatibility in assembly of the two chains. The human antibody sequences can be the sequences of naturally occurring human antibodies or can be consensus sequences of several human antibodies. See Carter et al., WO 92/22653. Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine 5C7.29 variable region framework residue and a selected human variable region framework residue, the human framework amino acid should usually be substituted by the equivalent framework amino acid from the mouse antibody when it is reasonably expected that the amino acid:

(1) contacts antigen directly, (2) is adjacent to a CDR region in the sequence, or (3) otherwise interacts with a CDR region (e.g., is within about 4–6 Å of a CDR region).

Other candidates for substitution are acceptor human framework amino acids that are unusual for a human immunoglobulin at that position. These amino acids can be substituted with amino acids from the equivalent position of the donor antibody or from the equivalent positions of more typical human immunoglobulins. The variable region frameworks of humanized immunoglobulins usually show at least 85% sequence identity to a human variable region framework sequence or consensus of such sequences.

(3) Human Antibodies

In another aspect of the invention, human antibodies cross-reactive with E-selectin and P-selectin are provided. These antibodies are produced by a variety of techniques described below. Some human antibodies are selected by competitive binding experiments, or otherwise, to have the same epitope specificity as an exemplified mouse antibody, such as 5C7.29. Such antibodies are particularly likely to share similar therapeutic properties.

a. Trioma Methodology

The basic approach and an exemplary cell fusion partner, SPAZ-4, for use in this approach have been described by Oestberg et al., *Hybridoma* 2:361–367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The B-lymphocytes are obtained from the blood, spleen, lymph nodes or bone marrow of a human donor. In vivo immunization of a living human with E-selectin and/or P-selectin is usually undesirable because of the risk of initiating a harmful response. Thus, B-lymphocytes are usually immunized in vitro with an E-selectin and/or P-selectin or an antigenic fragment of either of these, or a cell bearing either of these. Specific epitopic fragments consisting essentially of the amino acid segments that bind to one of the exemplified murine antibodies are preferred for in vitro immunization. B-lymphocytes are typically exposed to antigen for a period of 7–14 days in a media such as RPMI-1640 (see Engleman, supra) supplemented with 10% human serum.

The immunized B-lymphocytes are fused to a xenogeneic hybrid cell such as SPAZ-4 by well known methods. For example, the cells are treated with 40–50% polyethylene glycol of MW 1000–4000, at about 37 degrees, for about 5–10 min. Cells are separated from the fusion mixture and propagated in media selective for the desired hybrids (e.g., HAT or AH). Clones secreting antibodies having the required binding specificity are identified by assaying the trioma culture medium for the ability to bind to E-selectin and P-selectin using the same methods as discussed above for nonhuman antibodies. Triomas producing human antibodies having the desired specificity are subcloned by, e.g., the limiting dilution technique and grown in vitro in culture medium.

Although triomas are genetically stable they may not produce antibodies at very high levels. Expression levels can be increased by cloning antibody genes from the trioma into one or more expression vectors, and transforming the vector into a cell line such as the cell lines discussed, infra, for expression of recombinant or humanized immunoglobulins.

b. Transgenic Non-Human Mammals

Human antibodies crossreactive with P-selectin and E-selectin can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); Kucherlapati, WO 91/10741 (1991) (each of which is incorporated by reference in its entirety for all purposes). Transgenic mice are particularly suitable. Crossreacting P-selectin/E-selectin human antibodies are obtained by immunizing a transgenic nonhuman mammal, such as described by Lonberg or Kucherlapati, supra, according to the same strategy as discussed for a nontransgenic nonhuman animal (section I.C.(1)). Monoclonal antibodies are prepared by, e.g., fusing B-cells from such mammals to suitable myeloma cell lines using conventional Kohler-Milstein technology.

c. Phage Display Methods

A further approach for obtaining human crossreacting antibodies to E-selectin and P-selectin is to screen a DNA library from human B cells as described by Dower et al., WO 91/17271 and McCafferty et al., WO 92/01047 (each of which is incorporated by reference in its entirety for all purposes). In these methods, libraries of phage are produced in which members display different antibodies on their outer surfaces. Antibodies are usually displayed as Fv or Fab fragments. Phage displaying antibodies are selected by affinity enrichment for binding to either P-selectin or E-selectin. Phage identified by the initial screen are then further screened for crossreaction with the other ligand.

In a variation of the phage-display method, human antibodies having the binding specificity of a selected murine antibody can be produced. See Winter, WO 92/20791. In this method, either the heavy or light chain variable region of the selected murine antibody (e.g., 5C7.29) is used as a starting material. If, for example, a light chain variable region is selected as the starting material, a phage library is constructed in which members displays the same light chain variable region (i.e., the murine starting material) and a different heavy chain variable region. The heavy chain variable regions are obtained from a library of rearranged human heavy chain variable regions. A phage showing strong specific binding for P-selectin and E-selectin (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for P-selectin and E-selectin are selected. These phage display the variable regions of completely human antibodies that crossreact with E-selectin and P-selectin. These antibodies usually have the same or similar epitope specificity as the murine starting material (e.g., 5C7.29).

D. Bispecific Antibodies

The invention also provides bispecific or bifunctional antibodies that have one binding site that specifically binds to P-selectin and E-selectin and a second binding site that specifically binds to a second moiety. In bispecific antibodies, one heavy and light chain pair is usually from a crossreacting antibody and the other pair from an antibody raised against another epitope. This results in the property of multi-functional valency, i.e., ability to bind at least two different epitopes simultaneously, one of which is the epitope to which the anti P-selectin/E-selectin crossreacting antibody binds. The other epitope could be e.g., an epitope on L-selectin.

E. Other Therapeutic Agents

Having produced an antibody having desirable properties, such as 5C7.29 and the other exemplified antibodies, other non antibody agents having similar binding specificity/and or affinity can be produced by a variety of methods. For example, Fodor et al., U.S. Pat. No. 5,143,854, discuss a technique termed VLSIPS™, in which a diverse collection of short peptides are formed at selected positions on a solid substrate. Such peptides could then be screened for binding to an epitopic fragment recognized by 5C7.29, optionally in competition with the 5C7.29. Libraries of short peptides can also be produced using phage-display technology, see, e.g., Devlin WO91/18980. The libraries can be screened for binding to an epitopic fragment recognized by e.g., 5C7.29, optionally in competition with 5C7.29.

II. Nucleic Acids

The genes encoding the heavy and light chains of immunoglobulins produced by hybridoma or trioma cell lines secreting crossreacting antibodies are cloned according to methods described in Sambrook et al., *Molecular Cloning: A Laboratory Manual*, 2nd ed. (Cold Spring Harbor, N.Y., 1989); Berger & Kimmel, Methods in Enzymology, Volume 152, *Guide to Molecular Cloning Techniques* (Academic Press, Inc., San Diego, Calif., 1987); Co et al., *J. Immunol.* 148:1149 (1992). For example, genes encoding heavy and light chains are cloned from a hybridomals genomic DNA or cDNA produced by reverse transcription of RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a hybridoma or trioma cell line. Alternatively, DNA segments encoding only a portion of the primary antibody genes are produced, which portions possess binding and/or effector activities. Other recombinant constructs contain segments of immunoglobulin genes fused to segments of other immunoglobulin genes, particularly segments of other human constant region sequences (heavy and/or light chain). Human constant region sequences can be selected from various reference sources, including those listed in Kabat et al., supra.

DNA segments encoding crossreacting P-selectin/E-selectin antibodies can be modified by recombinant DNA techniques such as site-directed mutagenesis (see Gillman & Smith, *Gene* 8:81–97 (1979); Roberts et al., *Nature*, 328:731–734 (1987). Such modified segments will usually retain antigen binding capacity and/or effector function. Moreover, the modified segments are usually not so far changed from the original sequences to prevent hybridization to these sequences under stringent conditions. The modified segments will usually encode an immunoglobulin showing substantial sequence identity to a reference immunoglobulin from which it was derived. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

The recombinant polynucleotide constructs will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. Saccharomzyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, *From Genes to Clones*, (VCH Publishers, N.Y., 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see generally, Sambrook et al., supra).

Once expressed, crossreacting immunoglobulins of the invention can be purified according to standard procedures of the art, including HPLC purification, column chromatography, gel electrophoresis and the like (see generally, *Scopes, Protein Purification* (Springer-Verlag, N.Y., 1982)).

III. Epitope Mapping

The P-selectin epitope(s) bound by the 5C7.29 or other crossreacting antibody can be determined by providing a family of fragments containing different amino acid segments from P-selectin. Each fragment typically comprises at least 4, 6, 8, 10, 20, 50 or 100 contiguous amino acids. The family of polypeptide fragments cover much or all of the amino acid sequence of the extracellular domain of a P-selectin polypeptide. Members of the family are tested individually for binding to e.g., the 5C7.29 antibody. The smallest fragment that can specifically bind to the antibody being tested contains the amino acid sequence of the epitope recognized by the antibody. The E-selectin epitope bound by the antibody is mapped by an analogous strategy using a family of peptides from E-selectin. The respective epitopes on P-selectin and E-selectin are expected to map to segments of these molecules showing a high degree of sequence identity. The epitopic fragments are useful as immunogens for generating further crossreacting antibodies. The epitopic fragments are also useful as therapeutic agents that agonize or antagonize the function of P-selectin or E-selectin.

Another method to map epitopes involves testing the ability of an antibody to bind to E-selectin or P-selectin to which random mutations have been introduced. This method is described in more detail in Example 9.

IV. Pharmaceutical Compositions

The pharmaceutical compositions for use in the therapeutic methods discussed infra, typically comprise an active agent, such as crossreacting E-selectin/P-selectin antibody, dissolved in an acceptable carrier, preferably an aqueous carrier. Some compositions contain a cocktail of multiple active agents, for example, a crossreacting antibody and a thrombolytic agent. A variety of aqueous carriers can be used, e.g., water, buffered water, phosphate buffered saline (PBS), 0.4% saline, 0.3% glycine, human albumin solution and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride and sodium lactate. The concentration of antibody in these formulations can vary widely, i.e., from less than about 0.005%, usually at least about 1% to as much as 15 or 20% by weight and will be selected primarily based on fluid volumes, viscosities, and so forth, in accordance with the particular mode of administration selected.

Thus, a typical pharmaceutical composition for injection could be made up to contain 1 ml sterile buffered water, and 1–10 mg of immunoglobulin. A typical composition for intravenous infusion could be made up to contain 250 ml of sterile Ringer's solution, and 150 mg of antibody. Methods for preparing parenterally administrable compositions are described in *Remington's Pharmaceutical Science* (15th ed., Mack Publishing Company, Easton, Pa., 1980), which is incorporated by reference in its entirety for all purposes.

Therapeutic agents of the invention can be frozen or lyophilized for storage and reconstituted in a suitable carrier prior to use. Lyophilization and reconstitution can lead to varying degrees of antibody activity loss (e.g., with conventional immune globulins, IgM antibodies tend to have greater activity loss than IgG antibodies). Dosages may have to be adjusted to compensate.

V. Therapeutic Methods

The antibodies of the present invention are useful for treatment of inflammatory diseases and conditions, especially those which are mediated by neutrophils. The dual specificity of the antibodies leads to the inhibition of inflammatory events mediated by either P-selectin or E-selectin.

For example, the antibodies are suitable for therapeutic and prophylactic treatment of ischemia-reperfusion injury caused by myocardial infarction, cerebral ischemic event (e.g., stroke), renal, hepatic or splenial infarction, brain surgery, lung injury, shock, cardiac surgery (e.g., coronary artery bypass), elective angioplasty, and the like. Other preferred applications are the treatment of sepsis, adult respiratory distress syndrome, and multiple organ failure. The antibodies are also useful for treating injury due to trauma, burns, frostbite or damage to the spinal cord. The antibodies will also find use in treating autoimmune diseases including rheumatoid arthritis, systemic lupus erythematosus, multiple sclerosis, type I diabetes and uveitis, in treating inflammatory diseases of the skin such as psoriasis, and in treating meningitis and encephalitis. The antibodies are also useful for treating allergic rhinitis, asthma and anaphylaxis. Other typical applications are the prevention and treatment of organ transplant rejection and graft-versus-host disease.

The pharmaceutical compositions containing the antibodies are particularly useful for parenteral administration, i.e., subcutaneously, intramuscularly or intravenously. The antibodies of the invention may also be administered, typically for local application, by gavage or lavage, intraperitoneal injection, ophthalmic ointment, topical ointment, intracranial injection (typically into a brain ventricle), intrapericardiac injection, or intrabursal injection.

The compositions containing the present antibodies or a cocktail thereof can be administered for prophylactic and/or therapeutic treatments. In therapeutic applications, compositions are administered to a patient already suffering from an inflammatory disease, in an amount sufficient to cure or at least partially arrest the disease and its complications. An amount adequate to accomplish this is defined as a "therapeutically effective dose." Amounts effective for this use will depend upon the severity of the disease and the general state of the patient's own immune system, but generally range from about 1 to about 200 mg of antibody per dose, with dosages of from 5 to 80 mg per patient being more commonly used. Dosing schedules will vary with the disease state and status of the patient, and will typically range from a single bolus dosage or continuous infusion to multiple administrations per day (e.g., every 4–6 hours), or as indicated by the treating physician and the patient's condition. In life-threatening or potentially life-threatening situations, it is possible and may be felt desirable by the treating physician to administer substantial excesses of these antibodies.

In prophylactic applications, compositions containing the present antibodies or a cocktail thereof are administered to a patient not already suffering from a particular disease to enhance the patient's resistance. Such an amount is defined to be a "prophylactically effective dose." In this use, the precise amounts again depend upon the patient's state of health and general level of immunity, but generally range from 1 to 80 mg per dose. Preferred prophylactic uses are for the prevention of adult respiratory distress syndrome in patients already suffering from sepsis or trauma; prevention of organ transplant rejection; and prevention of reperfusion injury in patients suffering from ischemia. In seriously ill patients, dosages of about 50 to 150 mg of humanized or human immunoglobulin per administration are frequently used, and larger dosages may be indicated.

Single or multiple administrations of the compositions can be carried out with dose levels and pattern being selected by the treating physician. In any event, the pharmaceutical formulations should provide a quantity of the antibody(ies) of this invention sufficient to treat the patient effectively.

The antibodies can also be used in combination with other antibodies, particularly antibodies reactive with different adhesion molecules. For example, suitable antibodies include those specific for CD11a, CD11b, CD18, L-selectin, and ICAM-1. Other suitable antibodies are those specific for lymphokines, such as IL-1, IL-2 and IFN-γ, and their receptors. The antibodies of the invention can also be administered in conjunction with chemotherapeutic agents. Suitable agents include non-steroidal anti-inflammatory drugs and corticosteroids, but numerous additional agents (e.g., cyclosporin) can also be used.

In some therapeutic methods of ischemia-reperfusion therapy, crossreacting antibodies are used in combination with thrombolytic agents. In previous methods, patients with myocardial infarction or unstable angina are often treated by opening the occluded coronary artery. Reopening of the obstructed coronary artery can be achieved by administration of thrombolytic agents which lyse the clot causing the obstruction, and which, thereby, restore coronary blood flow. Reperfusion of the vessel can also be achieved by percutaneous transluminal coronary angioplasty (PTCA) by means of balloon dilation of the obstructed and narrowed segment of the coronary artery. However, restoration of coronary blood flow leads to ischemia-reperfusion injury in prior methods.

In the present methods, ischemia-reperfusion injury is reduced or prevented by combination of a thrombolytic agent or of PTCA with crossreacting E-selectin/P-selectin antibodies. Antibodies are usually administered prophylactically before, or at the same time as, administration of thrombolytic agents or initiation of PTCA. Further doses of antibody are then often administered during and after thrombolytic or angioplastic treatment. The interval between prophylactic administration of the antibodies and initiation of thrombolytic or angioplastic treatment is usually 5–60 mins, preferably 5–30 min, and most preferably 5–10 min. The antibodies are administered parentally, preferably by intravenous injection, in doses of 0.01–10 mg/kg body weight, preferably of 0.14–5 mg/kg and most preferably of 0.3–3 mg/kg. The antibodies can be given as an intravenous bolus injection, e.g., over 1–5 min., as repeated injections of smaller doses, or as an intravenous infusion. The bolus injection is especially useful for the prophylactic dose or in an emergency. Further doses of antibodies can be repeated (e.g., every 4–24 hr) during and after thrombolytic or angioplastic treatment of acute myocardial infarction at the same proportions as described above to achieve optimal plasma levels of the antibody.

Thrombolytic agents are drugs having the capacity, directly or indirectly, to stimulate dissolution of thrombi in vivo. Thrombolytic agents include tissue plasminogen activator (see EP-B 0 093 619), activase, alteplase, duteplase, silteplase, streptokinase, anistreplase, urokinase, heparin, warfarin and coumarin. Additional thrombolytic agents include saruplase and vampire bat plasminogen activator. See Harris, *Protein Engineering* 6:449–458 (1987); PCT/EP 90/00194; U.S. Pat. No. 4,970,159. Thrombolytic agents are administered to a patient in an amount sufficient to partially disperse, or prevent the formation of, thrombi and their complications. An amount adequate to accomplish this is defined as a "therapeutically effective dose" or "efficacious dose." Amounts effective for this use will depend upon the severity of the condition, the general state of the patient, the route of administration and combination with other drugs. Often, therapeutically effective doses of thrombolytic agents and administration regimens for such agents with crossreacting antibodies to E-selectin and P-selectin are those approved by the FDA for independent uses of thrombolytic agents, e.g., 100 mg of alteplase or 1.5 million IU of streptokinase.

VI. Methods of Diagnosis

The monoclonal antibodies of the present invention are useful for diagnosing the inflammatory conditions discussed above and monitoring the treatment thereof. The antibodies detect P-selectin and E-selectin in a tissue sample such as serum or endothelial cells, e.g., by ELISA or RIA. The presence of either selectin is diagnostic of inflammation. Selectin levels may be employed as a differentiation marker to identify and type cells of certain lineages and developmental origins.

In such procedures, the antibody can be labelled directly (e.g., by radioactive or fluorescent label) and immune complexes detected via the label. Usually, however, the antibody is unlabelled and the desired antigen-monoclonal antibody complex is detected with an enzyme-conjugated antibody against the monoclonal antibody. Diagnosis can also be achieved by in vivo administration of a labelled crossreacting P-selectin/E-selectin antibody and detection by in vivo imaging. The concentration of antibody administered should be sufficient that the binding to cells having the target antigen is detectable compared to the background signal. The diagnostic reagent can be labelled with a radioisotope for camera imaging, or a paramagnetic isotope for magnetic resonance or electron spin resonance imaging.

VII. Other Uses

The antibodies are also useful for affinity purification of selectins and cells expressing the same on their external surfaces. The antibodies can also be used. to generate anti-idiotypic antibodies that mimic a selectin domain responsible for antibody binding. Anti-idiotypic antibodies are useful as competitive inhibitors of selectin binding. For example, an anti-idiotypic antibody to a crossreacting P-selectin, E-selectin monoclonal antibody can be selected to compete with P-selectin and/or E-selectin for binding to their counterreceptors. The antibodies are also useful in screening for a therapeutic agent having the same binding specificity as a crossreacting antibody (see Section I. E).

The following examples are provided to illustrate but not to limit the invention:

EXAMPLE 1

Preparation of Cells Transfected With Selectins

L1-2 murine pre-B cell selectin transfectants are obtained by inserting the respective human selectin genes downstream of the LCMV promoter in pMRB101 or similar plasmid (pMRB101 is a derivative of EEb which contains the *E. coli* gpt gene. Mulligan et al., *Proc. Natl. Acad. Sci. USA* 78:2072–2076 (1981); Stephans et al., *Nucleic Acids Research* 17:7110 (1989)). Plasmid DNA is introduced into L1-2 cells by standard methods, such as electroporation, and the cells are selected for resistance to mycophenolic acid. Cells expressing high levels of the appropriate selectin are further selected by "panning" or fluorescence activated cell sorting techniques. See *Lymphocytes, A Practical Approach* (G.C.B. Klaus, IRL Press, Oxford, England, 1987).

EXAMPLE 2

Production of Crossreacting Monoclonal Antibodies

Crossreacting antibodies were produced using two different immunization procedures. In all of these procedures, the inoculum was $10^7$ L1-2 selectin transfectant cells (Berg et al., 1991, 1992, supra) in PBS per injection into mice. In one procedure, Balb/c mice at 4–6 weeks of age (Simonson Labs, Gilroy, Calif.) were injected IP with L1-2$^{E\text{-}selectin}$ transfectants at day 0 and day 14, and L1-2$^{P\text{-}selectin}$ transfectants at day 46, followed by fusion of spleen cells on day 50. In a second procedure, C57/Ld mice at 4–6 weeks of age (Jackson Labs, Bar Harbor, Me.) were immunized in the footpad with hypotonically lysed L1-2$^{E\text{-selectin}}$ cells on day 0, then with intact L1-2$^{E\text{-selectin}}$ cells on days 3 and 6, and with L1-2$^{P\text{-selectin}}$ cells on day 9. The draining lymph node lymphocytes were fused on day 12. In each procedure, mouse B-cells were fused with P3X mouse myeloma cells using polyethylene glycol.

Hybridoma supernatants were screened for specific binding to both E- and P-selectin by two-color FACS analysis. L1-2$^{P\text{-selectin}}$ and L1-2$^{control}$ transfectants were biotinylated by incubation with amino hexanoyl-biotin-N-hydroxy succinimide (Zymed Labs, South San Francisco, Calif.) at 10 μg/ml in PBS pH 8.0 for 25 min, at RT. After washing, 2×10$^7$ cells/ml were incubated with FITC-Z-Avidin (Zymed Labs, So. San Francisco, Calif.) diluted 1:150 for L1-2$^{P\text{-selectin}}$ cells and 1:1000 for L1-2$^{control}$ cells in FACS Buffer (2% BSA/PBS/10 mM NaN$_3$) for 30 min at 4° C. After washing, cells were mixed with unlabelled L1-2$^{E\text{-selectin}}$ cells at a 1:1:1 ratio in FACS Buffer. 50 μl hybridoma supernatants were added to 200,000 mixed cells in 50 μl in 96-well plates and incubated for 1 hr on ice. After washing, secondary agent was added, 50 μl of 1:500 Goat F(ab')2 anti-mouse IgG-PE conjugated (TAGO, Burlingame, Calif.) for 30 min prior to washing and fixation. FACS analysis was performed on a Becton Dickinson FACScan™ (San Jose, Calif.), according to standard procedures.

Supernatants containing antibodies reacting with both P-selectin and E-selectin were identified by a shift in red fluorescence of the L1-2$^{E\text{-selectin}}$ transfectant (unlabelled with FITC) and the brightest FITC labelled cells (L1-2$^{P\text{-selectin}}$ transfectants). The control L1-2 cells (moderately labelled with FITC) did not show a shift in red fluorescence, indicating that binding was specific for P-selectin and E-selectin. The yield of crossreacting antibodies as a ratio of supernatants screened was 1/844 and 2/57 for the two immunization schedules.

Supernatants showing binding to P-selectin and E-selectin transfectants were subcloned by limiting dilution and grown in serum free medium containing residual amounts of FBS. Three E-/P-selectin cross-reacting antibodies, designated 5C7.29, 1D8.10 and 2C9.11, were purified from these supernatants on Protein A-Sepharose™ (Pierce) according to the recommended protocol. Two antibodies reacting only with E-selectin, 1E4 and 2D4, and an antibody reacting only with P-selectin, 5F4, were identified by the same method. The isotypes of 5C7.29, 1D8.10, 2C9.11, 1E4, and 5F4 were determined to be IgG1, and that of 2D4 was determined to be IgG2a using an Innogenetics Inno-Lia mouse monoclonal antibody isotyping kit (Biosource International, Camarillo, Calif.).

Figure 1B:
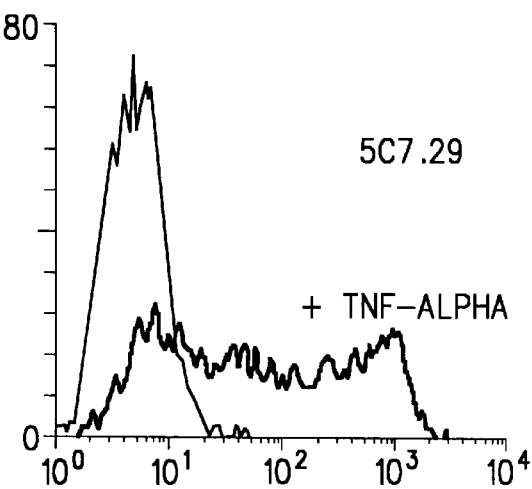

The three E-/P-selectin crossreacting-antibodies were also tested for their ability to bind to the natural ligands, rather than the recombinant forms used in the initial screening assays, by single color FACS analysis. The source of natural E-selectin used in these tests was TNF-α-activated human umbilical vein endothelial cells (HUVEC). In activated form, HUVEC cells express E-selectin, but do not express appreciable amounts of P-selectin. FIG. 1b shows that the E-/P-cross-reactive antibody 5C7.29 reacts with TNF-α activated HUVEC (shown by black histograms) but not unactivated HUVEC (grey histograms). Similar results were obtained for the two other cross-reacting antibodies 2C9.11 and 1D8.10. The activated cells also reacted with the anti-E-selectin blocking antibody H18/7 (FIG. 1a) (Becton Dickinson (San Jose, Calif.)), but not with P-selectin-specific antibodies WAPS 12.2 and 5F4. (WAPS 12.2, a P-selectin blocking antibody, was provided by R. Aaron Warnock and Eugene C. Butcher (Stanford, Calif.).)

Figure 2A:
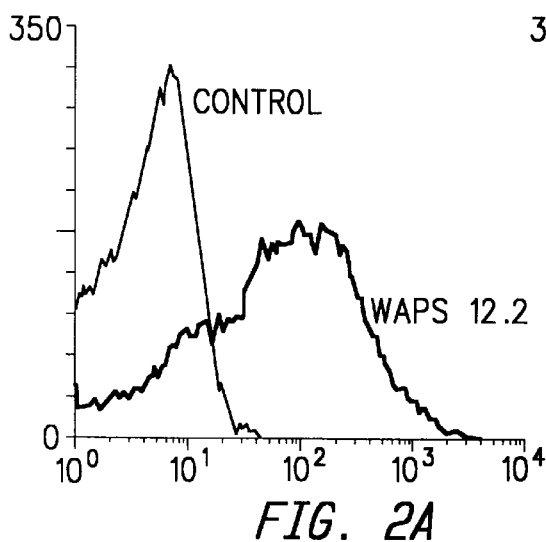
FIGS. 2A and 2B: Crossreacting antibody 5C7.29 binds to naturally occurring P-selectin. (a) Binding of known anti-P-selectin antibody WAPS 12.2 to platelets detected by staining with secondary antibody (black histogram), compared with staining with secondary antibody alone (control, grey histogram). (b) Binding of 5C7.29 to platelets, shown similarly.
Figure 2B:
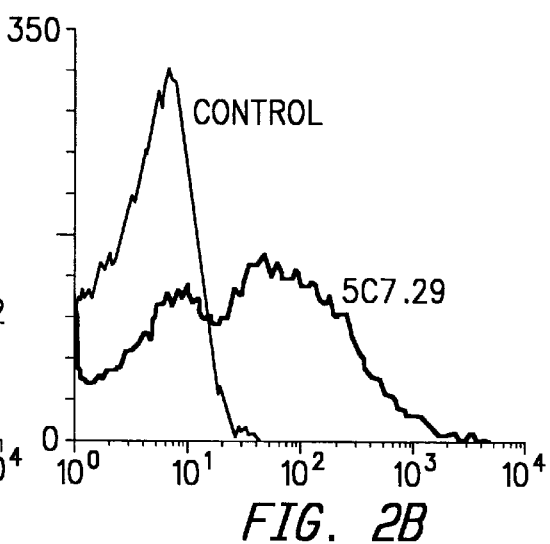

The source of natural P-selectin used in these tests was thrombin-activated platelets. FIG. 2b shows that 5C7.29 binds to these cells as does the known P-selectin antibody WAPS 12.2 (FIG. 2a). Similar results were obtained with 2C9.11 and 1D8.10. Platelets did not significantly react with anti-E-selectin antibodies H18/7 or 1E4.

The E-/P-selectin crossreacting antibodies were further analyzed for binding to L1-2$^{L\text{-selectin}}$ transfectants, and with normal human lymphocytes. Specific binding was not observed, demonstrating that the antibodies are specific for E- and P-selectins and do not bind to L-selectin.

To confirm that the crossreacting antibodies were truly monoclonal, preclearing experiments were performed. 10 ng antibody (a limiting amount) was incubated with a large number (10$^7$) of L1-2$^{E\text{-selectin}}$ cells or L1-2$^{P\text{-selectin}}$ cells for 1 hr. The supernatant was then transferred to a second aliquot of L1-2$^{E\text{-selectin}}$ cells or L1-2$^{P\text{-selectin}}$ cells (the same cell type as before) and incubated for 1 hr. Supernatant was transferred to a third aliquot of cells of the same type as before for a further 1 hr incubation. Supernatant was then removed and examined for reactivity with L1-2$^{E\text{-selectin}}$, L1-2$^{P\text{-selectin}}$ or L1-2 untransfected cells by one-color FACS analysis.

Figure 3A:
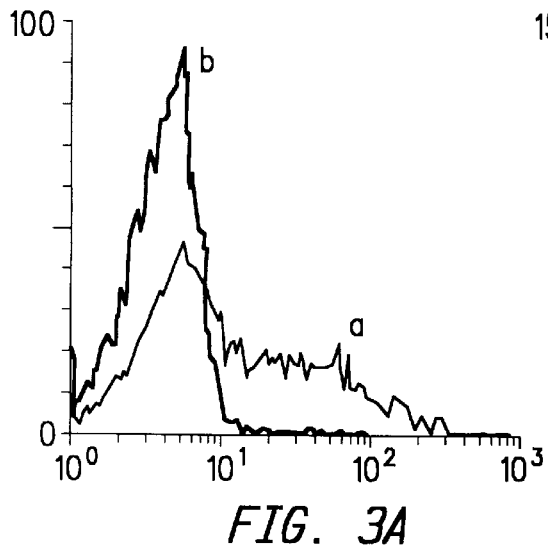
FIGS. 3A–B: Crossreactivity of 5C7.29 resides in a single monoclonal antibody. 5C7.29 antibody was incubated with excess of (a, c) parent L1-2 cells or (b, d) L1-2$^{P\text{-selectin}}$ transfectants, and resulting supernatants tested for reactivity with fresh samples of L1-2$^{P\text{-selectin}}$ (a, b) or L1-2$^{E\text{-selectin}}$ cells (c, d) by FACS analysis. These figures show that L1-2$^{P\text{-selectin}}$ depletes reactivity for E-selectin.
Figure 3B:
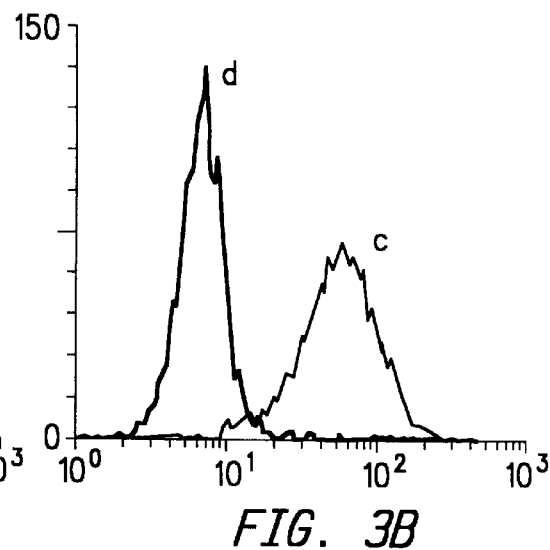

FIG. 3 shows that preincubation of a solution of the 5C7.29 antibody with L1-2$^{P\text{-selectin}}$ transfectants eliminated subsequent reactivity for both P-selectin and E-selectin. Similar results were found following preincubation with L1-2$^{E\text{-selectin}}$ transfectants. These results would be obtained only if the antibody bound to both selectins, and not if the antibody were a mixture of two different antibodies, one reactive with E-selectin and one reactive with P-selectin. Therefore, the dual specificities of 5C7.29 reside in the same antibody. Similar results were obtained for the 2C9.11 and 1D8.10 antibodies.

EXAMPLE 3

Inhibition of E-Selectin-Mediated Functions

The antibody 5C7.29 was tested for the ability to block E-selectin mediated functions. In one assay, the antibody was tested for inhibition of HL-60 binding to tumor necrosis factor-α (TNF-α) activated human umbilical vein endothelial cells (HUVEC). This binding assay simulates the binding of neutrophils to endothelial cells in an inflammatory response. The HL-60 cells are a promyelocytic cell line derived from a patient with acute promyelocytic leukemia. Collins et al., Nature 270, 347–349 (1977). The HUVEC cells are endothelial cells that when activated with TNF-α for 4–6 hours express E-selectin, and not P-selectin.

HUVEC were obtained from Clonetics (San Diego, Calif.) and cultured as suggested. Confluent cultures, up to passage 6, grown in 8 well plastic Lab Tek slides (Nunc, Naperville, Ill.) were activated for 4 hours with 1 ng/ml TNF-α (R&D Systems, Minneapolis, Minn.). HUVEC cultures were washed and incubated in 0.15 ml Assay Buffer (10% normal bovine serum/10% normal rabbit serum/10 mM HEPES, pH 7.2/RPMI) containing antibodies at 17 μg/ml (i.e., in excess) for 20 min.

HL-60 cells were fluorescently labelled with 6-carboxyfluorescein diacetate acetoxy-methyl ester (CFDA-AM, Molecular Probes, Eugene OR) (von Andrian et al., 1991, supra) by a 30 min incubation in 10 mg/ml RPMI/10 mM HEPES, pH 7.2, washed and resuspended in Assay Buffer and incubated at RT for 20 min. The resuspended cells (6×10⁵ cells in 0.15 ml) were then added to the HUVEC cultures.

Slides were rotated at 50 rpm on a rotator (Innova 200, New Brunswick Inc.) for 15 min at RT. The cover slips were removed and non-adherent HL-60 cells washed off by dipping slides in DMEM. Adherent cells were fixed by immersion in 1% paraformaldehyde-PBS. Slides were examined microscopically and the number of bound cells per field determined. Two treatments per slide (in quadruplicate) were analyzed.

Figure 4:
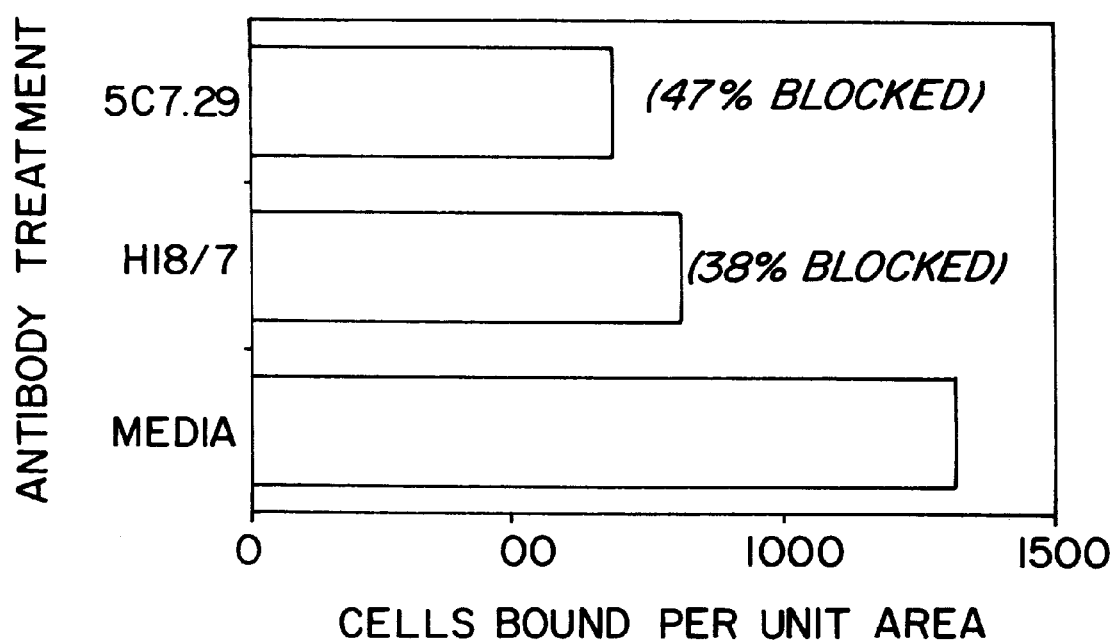
FIG. 4: Monoclonal antibody 5C7.29 blocks binding of HL-60 (neutrophil-like) cells to TNF-α-activated HUVEC cells (expressing E-selectin). Average of four experiments.

FIG. 4 shows that the number of HL-60 cells binding to the activated HUVEC was decreased 47% by preincubation with 5C7.29. This compared favorably with blocking by the anti-E-selectin-specific antibody H18/7 (38%). Binding was not significantly reduced by a control antibody.

Figure 5:
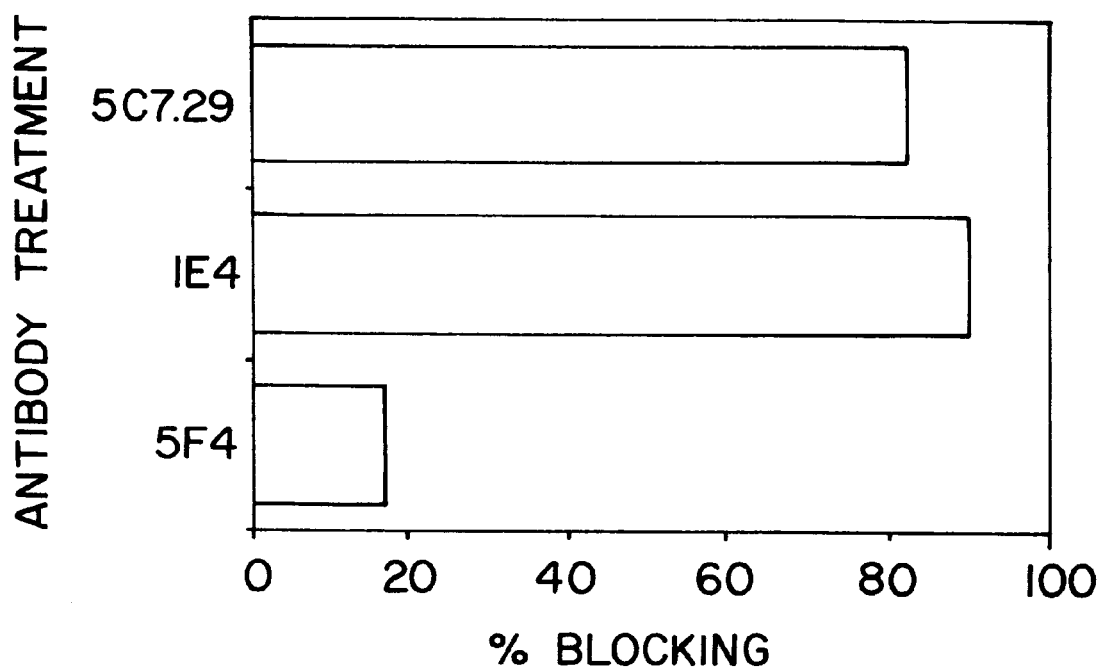
FIG. 5. Monoclonal antibody 5C7.29 blocks binding of HL-60 cells to E-selectin transfectant cells. Average of four experiments.

Because HUVEC can also express P-selectin (although only at low levels under the present activation conditions), 5C7.29 was also tested for HL-60 binding to CHO cells transfected with E-selectin. CHO cells permanently transfected with a truncated form of E-selectin containing the first four N-terminal domains of E-selectin fused to the transmembrane and cytoplasmic domain of another protein were produced according to standard methods. Expression was confirmed by reactivity with a control anti-E-selectin antibody (H18/7). Inhibition of binding between fluorescently labelled HL-60 and the transfected CHO cells was performed using the same assay as for the TNF-α-activated HUVEC. 5C7.29 was found to block adhesion by 82% (FIG. 5). Similar results were observed with 1D8.10, 2C9.11 and the E-selectin blocking antibody 1E4. The non-blocking P-selectin specific control antibody 5F4 had no significant effect in this assay.

The cross-reacting antibodies also blocked normal human peripheral blood neutrophil binding to TNF-α-activated HUVEC. At a final concentration of 10 μg/ml, 5C7.29 blocked 71 +/−13%, 2C9.11 blocked 62 +/−8% and 1D8 blocked 52 +/−10% of neutrophil binding to activated HUVEC, while the anti-E-selectin antibodies 1E4 and H18/7 (Bevilacqua et al., 1987, supra) blocked 68 +/−4% and 68 +/−15%, and a control mouse IgG1 antibody did not block (−21% +/−11%), n=4. For these experiments, neutrophils were isolated from normal human blood by density gradient centrifugation and dextran sedimentation by standard procedures (Current Protocols in Immunology, Coligan et al., eds., John Wiley and Sons, New York, 1992). Assays were performed as for HL-60 cells except neutrophils were added to HUVEC at 7.5×10⁴ in 0.15 ml.

EXAMPLE 4

Inhibition of P-selectin-Mediated Functions

The antibodies 5C7.29, 2C7.11 and 1D8.10 were tested for their ability to block P-selectin-mediated functions. Blocking was tested in a platelet-HL-60 rosette assay (Corral et al., 1990, supra). The platelets provide a source of cells expressing P-selectin and the HL-60 cells simulate neutrophils. Normal human blood was collected with sodium citrate as anticoagulant and the platelet-rich plasma (PRP) prepared by centrifugation at 250g for 10 min. Platelets were isolated from PRP by centrifugation at 100 g for 20 min and resuspended at 3×10⁸/ml in PBS, pH 7.2. Monoclonal antibodies (1 μg in 20 μl, i.e., an excess) were added to 20 μl platelets. In some experiments normal human thrombin (0.3 U/μl) was added to activate the platelets as described by Corral et al., 1990, supra. After 45 min, 20 μl HL-60 cells (10⁶/ml in PBS) were added and further incubated for 45 min. Bound platelets were fixed to HL-60 cells by addition of glutaraldehyde to 1.25%. At least 100 HL-60 cells for each sample were observed microscopically and the number of cells with bound platelets (>2 platelets per HL-60 cell) determined.

Figure 6:
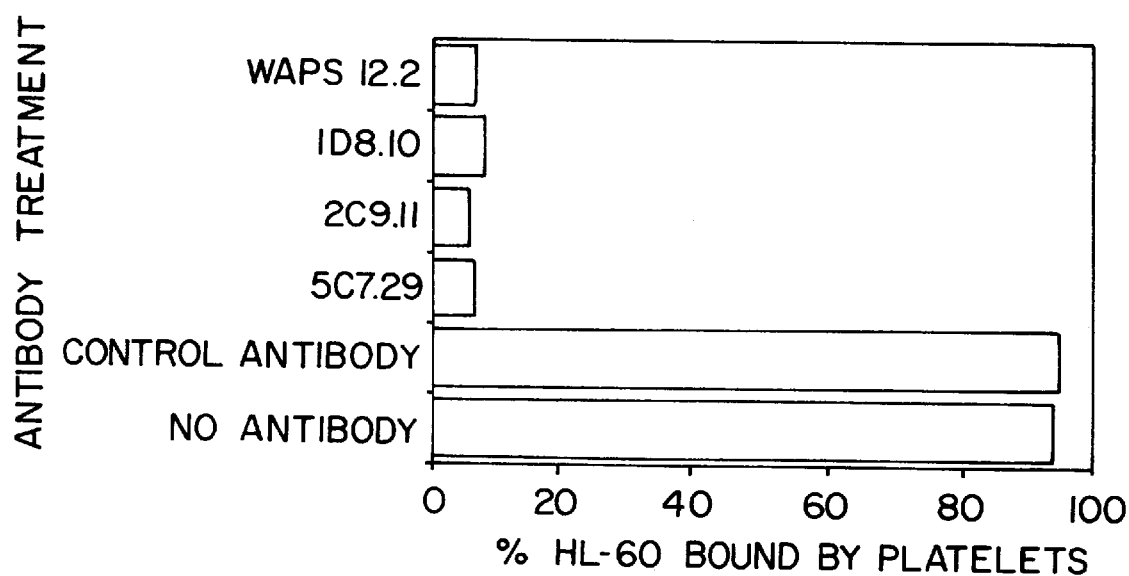
FIG. 6. Monoclonal antibodies 5C7.29, 2C9.11 and 1D8.10 block binding of platelets to HL-60 cells as shown by platelet rosetting. The chart shows the percentage of HL-60 cells with >2 platelets bound (rosetted). Average of three experiments.

FIG. 6 shows that all three crossreacting antibodies block rosetting to about the same extent as the P-selectin specific blocking antibody WAPS 12.2. Similar blocking experiments can be performed using human peripheral blood neutrophils in place of HL-60 cells. Neutrophils are prepared by the same method and used at the same concentration as described in Example 3.

EXAMPLE 5

Cloning and Sequencing of Mouse 5C7.29 Heavy Chain and Light Chain Variable Region cDNA cDNAs for the heavy chain and light chain variable region genes of the mouse 5C7.29 antibody were cloned using anchored polymerase chain reactions as described (see Co et al., J. Immunol. 148: 1149 (1992)), using 3' primers that hybridized to the constant regions and contained HindIII sites, and 5' primers that hybridized to the dG tails and contained EcoRI sites. The PCR amplified fragments were digested with EcoRI and HindIII and cloned into the pUC18 or pUC19 vectors for sequencing. At least two gamma-1 specific and two kappa specific clones were sequenced. The gamma-1 clones and the kappa clones are respectively identical in sequence. The variable region cDNA sequences and the deduced amino acid sequences for the gamma-1 and kappa chains are shown in FIGS. 7A–7B [SEQ ID NOS:1–4].

EXAMPLE 6

Design of Humanized 5C7.29 Antibody Variable Domain

Based on a sequence homology search against the NBRF protein sequence database, the variable regions of light chain subclass I and heavy chain subclass III show good homology to the mouse 5C7.29 antibody. In particular, the antibody III-3R provides the best framework homology with 5C7.29 and was chosen to provide the framework sequences for humanization of 5C7.29. However, other members of the light chain subclass I and heavy chain subclass III would also be especially suitable for use in providing the frameworks of the respective humanized 5C7.29 chains.

The computer program ENCAD (M. Levitt et al., J. Mol. Biol. 168: 595 (1983)) was used to construct a molecular model of the 5C7.29 variable domain. The program ABMOD (B. T. Zilber et al. Biochem. 29:10032–41) is also useful. The model was used to determine the amino acids in the 5C7.29 framework that were close enough to the CDRs to potentially interact with them. To design the humanized light and heavy chain 5C7.29 variable regions, the CDRs from the mouse 5C7.29 antibody were grafted into the framework sequences of the III-3R antibody. At framework positions where the model suggested contact with the CDRs, the amino acids from the mouse 5C7.29 antibody were chosen to replace the residues in the III-3R sequence. For humanized 5C7.29, this was done at residues 69 and 70 in the light chain and at no residues in the heavy chain. Moreover, at some positions where the amino acid was unusual for human antibodies at that position, an amino acid representing a consensus among the relevant human subclass was substituted for the III-3R framework residue. For humanized 5C7.29, this was done at residues 61, 72, 82 and 99 in the light chain and residues 1, 75 and 78 in the heavy chain.

The final sequence of the humanized 5C7.29 heavy and light chain variable region is shown in FIGS. 8A–8B [SEQ ID NOS:5–8]. However, many of the potential CDR-contact residues are amenable to substitutions of other amino acids and may still allow the antibody to retain substantial affinity to the antigens. The following table lists a number of positions in the framework where alternative amino acids may be suitable (note LC=light chain, HC=heavy chain):

TABLE 1

| Position | Humanized 5C7.29 | Alternatives |
| --- | --- | --- |
| LC-1 | D | Q |
| LC-3 | Q | V |
| LC-4 | M | L |
| LC-59 | S | A |
| LC-69 | S | D |
| LC-70 | Y | F |
| HC-49 | A | S |
| HC-84 | N | T |

Likewise, many of the framework residues not contacting the CDRs in the humanized 5C7.29 heavy and light chains are also amenable to substitutions with amino acids from either the human III-3R antibody, or from the corresponding position of other human antibodies, or from the mouse 5C7.29 or other mouse antibodies, while still preserving substantial affinity and non-immunogenicity of the humanized antibody. The following table lists a number of positions in the framework where alternative amino acids may be suitable:

TABLE 2

| Position | Humanized 5C7.29 | Alternatives |
| --- | --- | --- |
| LC-61 | F | I |
| LC-72 | L | F |
| LC-82 | F | I, A |
| LC-99 | Q | G, S |
| HC-1 | E | Q, D |
| HC-75 | S | A, P |
| HC-78 | T | S |
| HC-116 | A | S |

Finally, even certain residues in the CDRs may be substituted with other residues while the antibody may retain substantially the same affinity and specificity. Structure-function studies of antibody binding reveal that not all of the CDR amino acids participate equally in specifying affinity towards a given antigen (or set of related antigens). These studies enable prediction with some reliability of particular CDR positions least likely to change substantially the binding characteristics of an antibody. For example, Chothia and co-workers define structurally acceptable amino acids in CDR positions (Chothia et al., *J. Mol. Biol.* 196: 902 (1987); Chothia et al., *Nature* 342: 877 (1989); and Tramontano et al., *Proteins: Struct. Funct. Genet.* 6: 382 (1989)), and many of these are not accessible to solvent (i.e, available to participate in binding), in the model of 5C7.29. Other workers have shown that residues 61–66 of CDR H2 may not participate in antigen binding (Carter et al., *Proc. Natl. Acad. Sci. USA* 89: 4285 (1992); Hsiao et al., *Protein Eng.* 7:815 (1994)). Surveys of antibody-antigen complex structures support this notion (Glaser et al., *J. Immunol.* 149: 2606 (1992); Padlan, *Mol. Immunol.* 31: 169 (1994)). Some of these CDR residues that may be changed in humanized 5C7.29 and their potential substitutions are listed in the following table:

TABLE 3

| CDR | Position | Humanized 5C7.29 | Alternatives |
| --- | --- | --- | --- |
| L1 | 29 | V | I, L |
|  | 32 | M | L |
| L2 | 53 | L | any |
|  | 54 | A | any |
|  | 55 | S | T |
| L3 | 88 | Q | N, H |
|  | 89 | Q | N, H |
| H1 | 34 | M | I, V, L |
| H2 | 61 | A | any |
|  | 62 | D | any |
|  | 63 | T | any |
|  | 64 | V | A, I, L, M, F |
|  | 65 | R | K, Q |
|  | 66 | G | A, D, T, S |

Selection of various combinations of alternative amino acids may be used to produce versions of humanized 5C7.29 that have varying combinations of affinity, specificity, non-immunogenicity, ease of manufacture and other desirable properties. The above examples are offered by way of illustration, not of limitation.

EXAMPLE 7

Construction of Humanized 5C7.29

For the construction of variable region genes for the humanized 5C7.29 antibody, nucleotide sequences were selected that encode the protein sequences of the humanized heavy and light chains, including the signal peptide, generally utilizing codons found in the mouse sequence. Several degenerate codons were changed to create restriction sites or to remove undesirable ones. The nucleotide sequences of the genes also included splice donor signals and an XbaI site at each end. The nucleotide sequences and encoded light and heavy chain variable regions of the humanized 5C7.29 antibody are shown in FIGS. 8A–8B [SEQ ID NOS:5–8].

Figure 9:
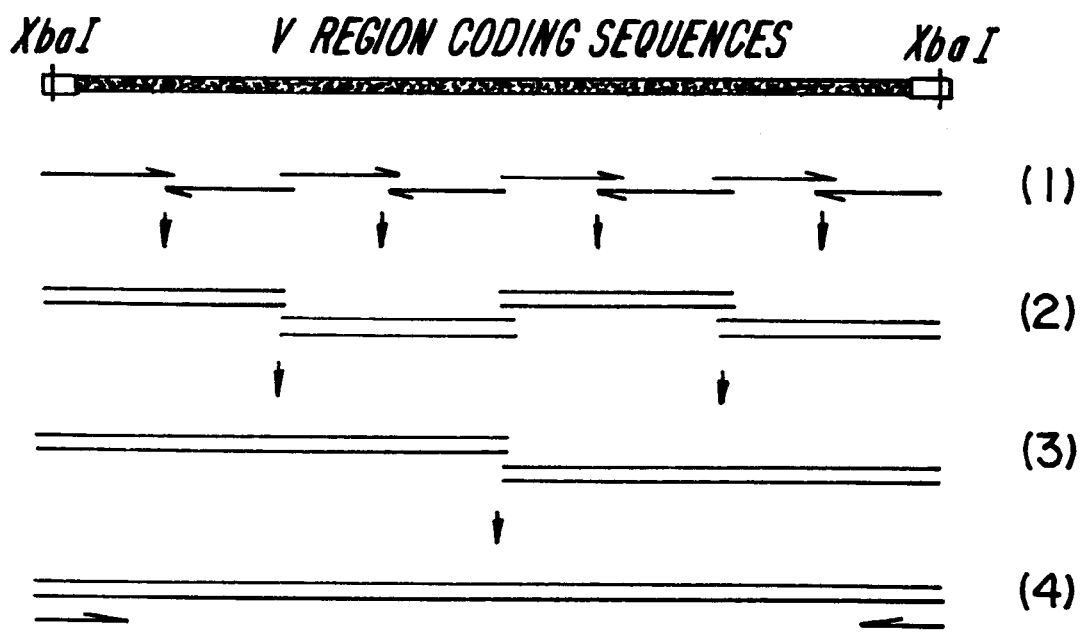
FIG. 9. Schematic diagram of construction of humanized 5C7.29 antibody variable region genes.

Each gene was constructed from eight overlapping synthetic oligonucleotides. Assembly and amplification of the genes were carried out in four steps as shown in FIG. 9: (1) the four pairs of complementary oligonucleotides were annealed and extended with Klenow polymerase in separate reactions; (2) the resulting four double-stranded DNA fragments were mixed in pairs, denatured, re-annealed and extended in two separate reactions using Klenow fragment; (3) the resulting two double-stranded half-gene fragments were mixed, denatured, re-annealed and extended to create the full length double stranded variable region genes; (4) the gene fragments were finally amplified, using Taq polymerase and two primers that hybridize to the 5′ and the 3′ end of the variable region genes and contain XbaI sites for cloning into the respective expression vectors, pVk and pVg4. Reactions were carried out under conditions well-known in the art.

The pVk vector for light chain expression and the pVg1 vector for heavy chain expression have been previously described (see Co et al., *J. Immunol.* 148: 1149 (1992)). To produce a humanized 5C7.29 antibody of the IgG4 isotype, the heavy chain expression vector pVg4 has been constructed. To do so, the XbaI-BamHI fragment of pVg1 containing the γ1 constant region was replaced with an approximately 2000 bp fragment of the human γ4 constant region gene (Ellison and Hood, *Proc. Natl. Acad. Sci USA* 79:1984 (1982)) that extended from the HindIII side preceding the CH1 exon of the γ4 gene to 270 bp after the NsiI site following the CH4 exon of the gene, using methods well-known to those skilled in the art, including polymerase chain reaction.

The heavy chain and light chain plasmids were transfected into a mouse myeloma cell line Sp2/0-Ag14 (ATCC CRL 1581). Transfection was by electroporation using a Gene Pulser apparatus (Bio-Rad) at 360 V and 25 uFD capacitance according to the manufacturer's instructions. Before transfection, the light chain- and heavy chain-containing plasmids were linearized using PvuII, extracted with phenol-chloroform, and ethanol-precipitated. All transfections were done using 30–50 μg plasmid DNA and about $10^7$ cells in PBS. The cells from each transfection were plated into 2 to 4 96-well tissue culture plates. After 48 hours, selective medium was applied.

Cells were selected for gpt expression in DMEM+10% FBS+HT media supplement (Sigma)+1 μg/ml mycophenolic acid. Antibody-producing clones were screened by assaying human antibody production in the culture supernatant by ELISA. Antibody from the best-producing clones was purified by passing tissue culture supernatant over a column of protein A-Sepharose™ CL-4B (Pharmacia). The bound antibodies were eluted with 0.2 M glycine-HCl, pH 3.0, and neutralized with 1 M Tris-HCl, pH 8.0. The buffer was exchanged into phosphate buffered saline (PBS) by passing over a PD10 column (Pharmacia), or by dialysis. To obtain cells producing higher levels of antibody, the transfected clones may be cultured in increasing concentrations of methotrexate.

EXAMPLE 8

Properties of Humanized 5C7.29

Figure 10:
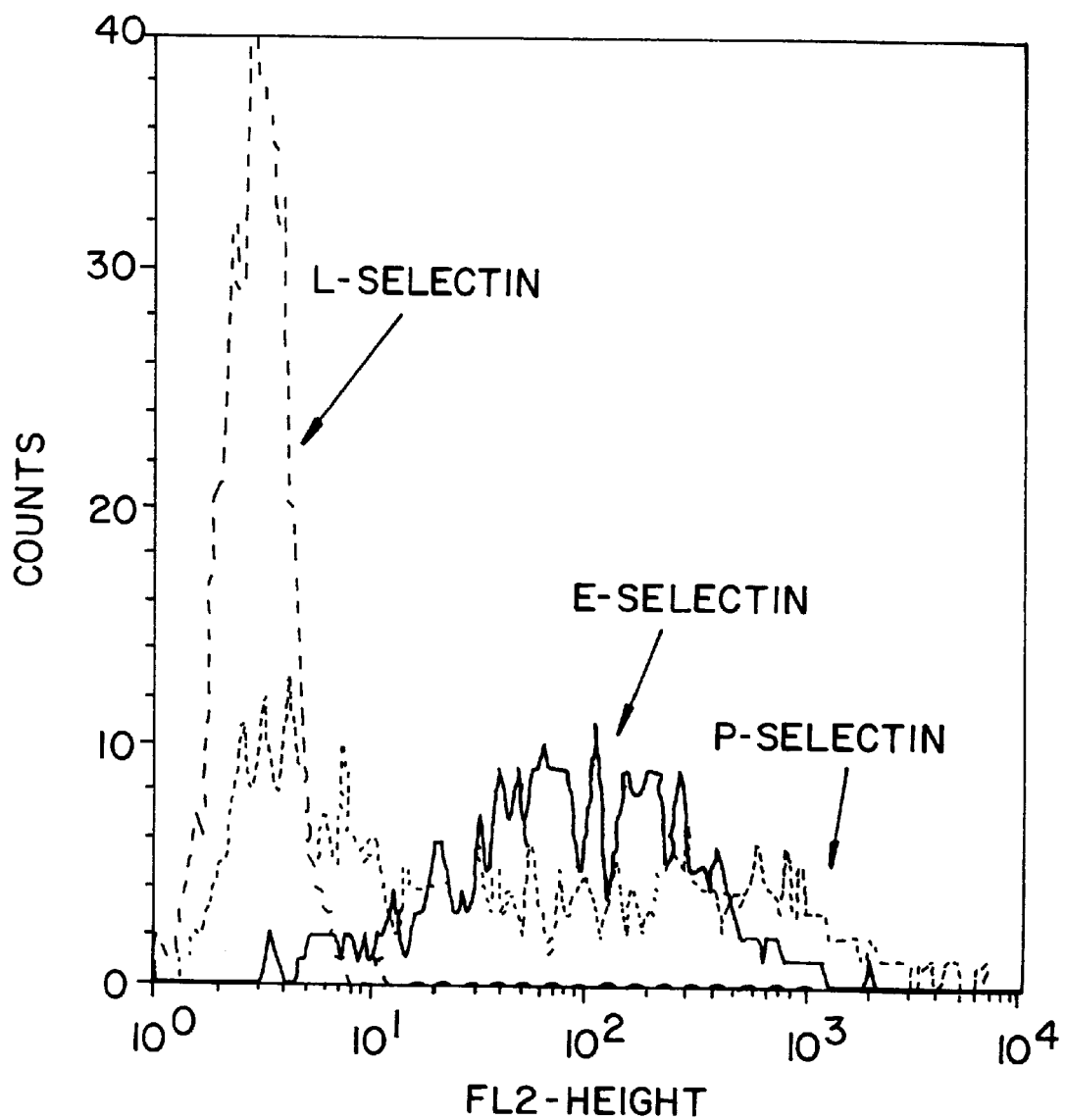
FIG. 10. Humanized 5C7.29 antibody reactivity with E-selectin, P-selectin and L-selectin transfectants. L1-2 transfectant cell lines expressing the indicated selectin were analyzed for reactivity with humanized 5C7.29 by flow cytometry.

To show that humanized 5C7.29 specifically binds to E-selectin and P-selectin, $L1-2^{E\text{-}selectin}$ and $L1-2^{P\text{-}selectin}$ transfectants were incubated with humanized 5C7.29 or control antibodies for 1 hour. After washing, cells were incubated in a 1:400 dilution of phycoerythrin-conjugated anti-human Ig (Biosource, Camarillo, Calif.), washed, then analyzed for fluorescence by flow cytometry (FACS) as previously described (Berg et al., *Blood* 85: 31 (1995)). Humanized 5C7.29 reacts with both $L1-2^{E\text{-}selectin}$ and $L1-2^{P\text{-}selectin}$ transfectants, but not $L1-2^{L\text{-}selectin}$ transfectants (FIG. 10) demonstrating that the humanization process did not result in loss of either E-selectin or P-selectin binding or gain in the ability to bind L-selectin.

Figure 11B:
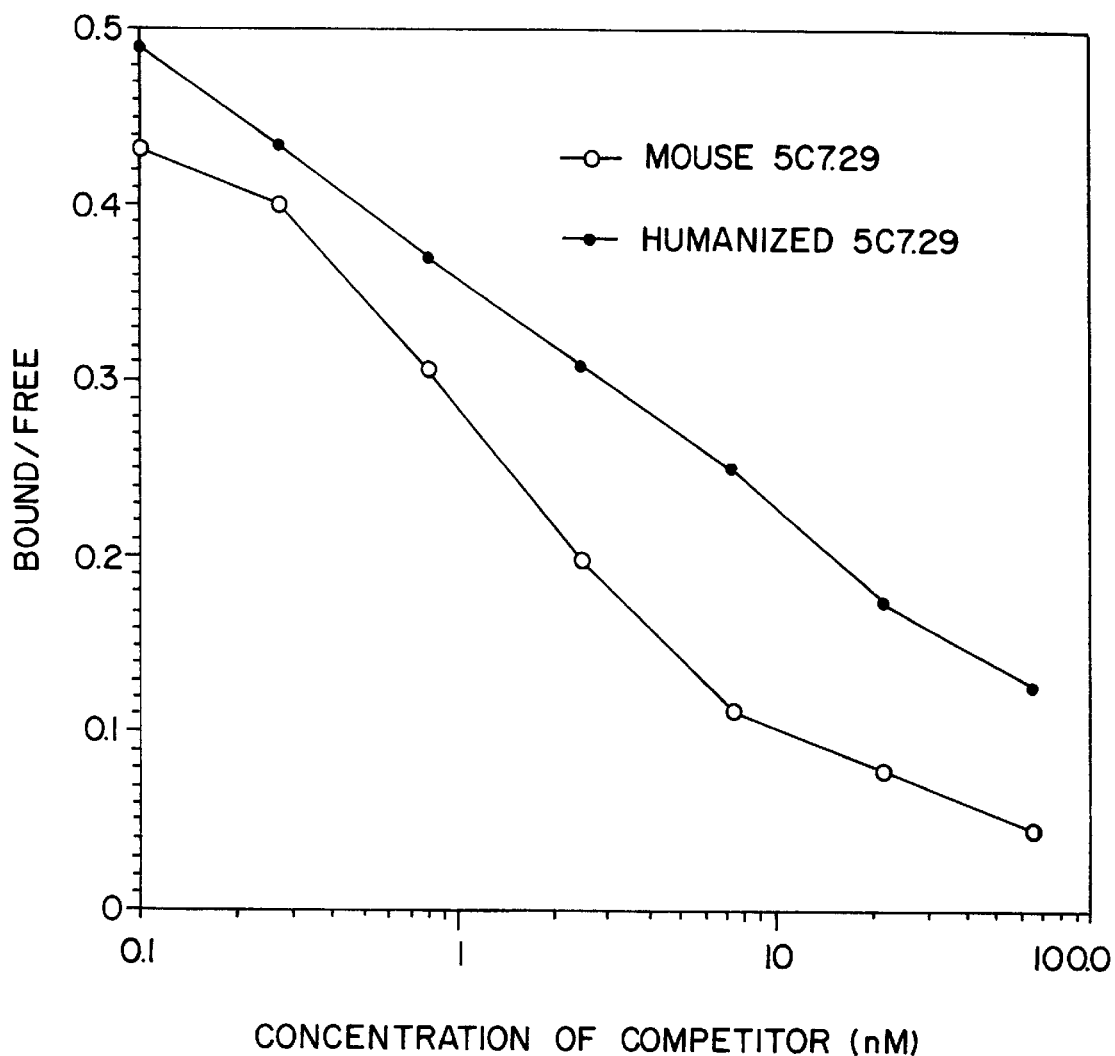

The affinity of the humanized 5C7.29 antibody for E-selectin and P-selectin was separately determined by competition with the radio-iodinated mouse 5C7.29 antibody (FIG. 11). Purified mouse 5C7.29 antibody was labeled with $Na^{125}I$ (Amersham, Arlington Heights, Ill.) using the lactoperoxidase procedure to 4 mCi/mg of protein. $CHO^{E\text{-}selectin}$ cells and $L1-2^{P\text{-}selectin}$ cells, which were obtained by transfecting the E-selectin and P-selectin genes into the respective host cells CHO and L1-2 (Gallatin et al., *Nature* 304:30 (1983)) by methods well known in the art (see, e.g., Larsen et al., *J. Biol. Chem.* 267: 11104 (1992)), were used as sources for E-selectin and P-selectin. Increasing amounts of competitor antibody (mouse 5C7.29 or humanized 5C7.29) were added to 2 ng of radio-iodinated tracer mouse 5C7.29 antibody and incubated with $4\times10^5$ $CHO^{E\text{-}selectin}$ cells or $L1-2^{P\text{-}selectin}$ cells in 0.2 ml of binding buffer (PBS with 2% fetal calf serum, 0.1% sodium azide) for 2 hours at 4° C. with constant shaking. Cells were then washed and centrifuged, and their radioactivities measured. The ratio of bound and free tracer antibody were calculated (FIGS. 11A and 11B).

The binding affinities were calculated according to the methods of Berzofsky and Berkower (J. A. Berzofsky and I. J. Berkower, in *Fundamental Immunology* (ed. W. E. Paul), Raven Press (New York), p. 595 (1984)). The humanized 5C7.29 had an affinity of approximately $3\times10^8$ $M^{-1}$ for E-selectin, with no significant difference from that of mouse 5C7.29, and an affinity of approximately $1.3\times10^8$ $M^{-1}$ for P-selectin, within about 3 to 4-fold of the mouse 5C7.29 antibody. This experiment also shows directly that humanized 5C7.29 has the ability to compete with the mouse 5C7.29 antibody for binding to both E-selectin and P-selectin. In another experiment, the affinities of mouse and humanized 5C7.29 for P-selectin were determined by the method of Scatchard (Berzofsky and Berkower, supra) to be approximately $1.9\times10^8$ $M^{-1}$ and $6\times10^8$ $M^{-1}$, respectively, in good agreement with the results of the competitive binding experiment.

Figure 12:
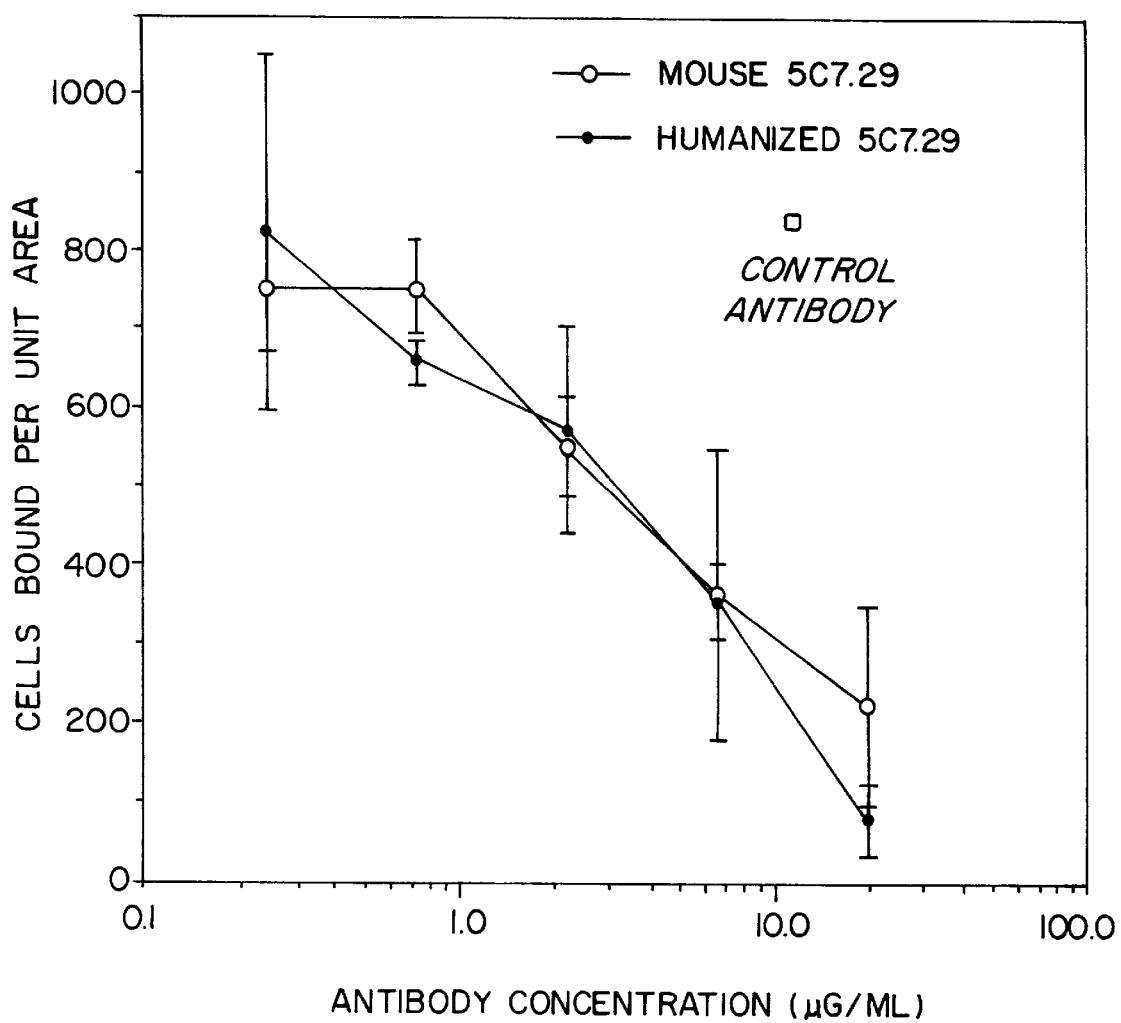
FIG. 12. Inhibition of HL-60 cell adhesion to CHO$^{E\text{-selectin}}$ cells by mouse and humanized 5C7.29 antibodies. Fluorescently labelled HL-60 cells were incubated with CHO$^{E\text{-selectin}}$ cells in the presence of the antibodies at the indicated concentrations. After washing, adherent cells were counted microscopically. The results from a representative experiment performed with each sample in quadruplicate (+/−standard deviation) are shown.

To show that the humanized 5C7.29 antibody inhibits binding of E-selectin to a counter-receptor for E-selectin, its ability to inhibit the binding of HL-60 cells to E-selectin transfectant cells was determined. Assays of the adhesion of HL-60 cells with $CHO^{E\text{-}selectin}$ cells were performed as previously described (Berg et al., *Blood* 85: 31 (1995), and supra) in the presence of monoclonal antibodies at the indicated concentrations. FIG. 12 shows that humanized 5C7.29 blocks binding of HL-60 cells to $CHO^{E\text{-}selectin}$ transfectants as well as mouse 5C7.29. For the representative experiment shown, two treatments per slide (each treatment in quadruplicate) were analyzed and the mean and standard deviations calculated. An isotype-matched control antibody did not affect binding.

Figure 13:
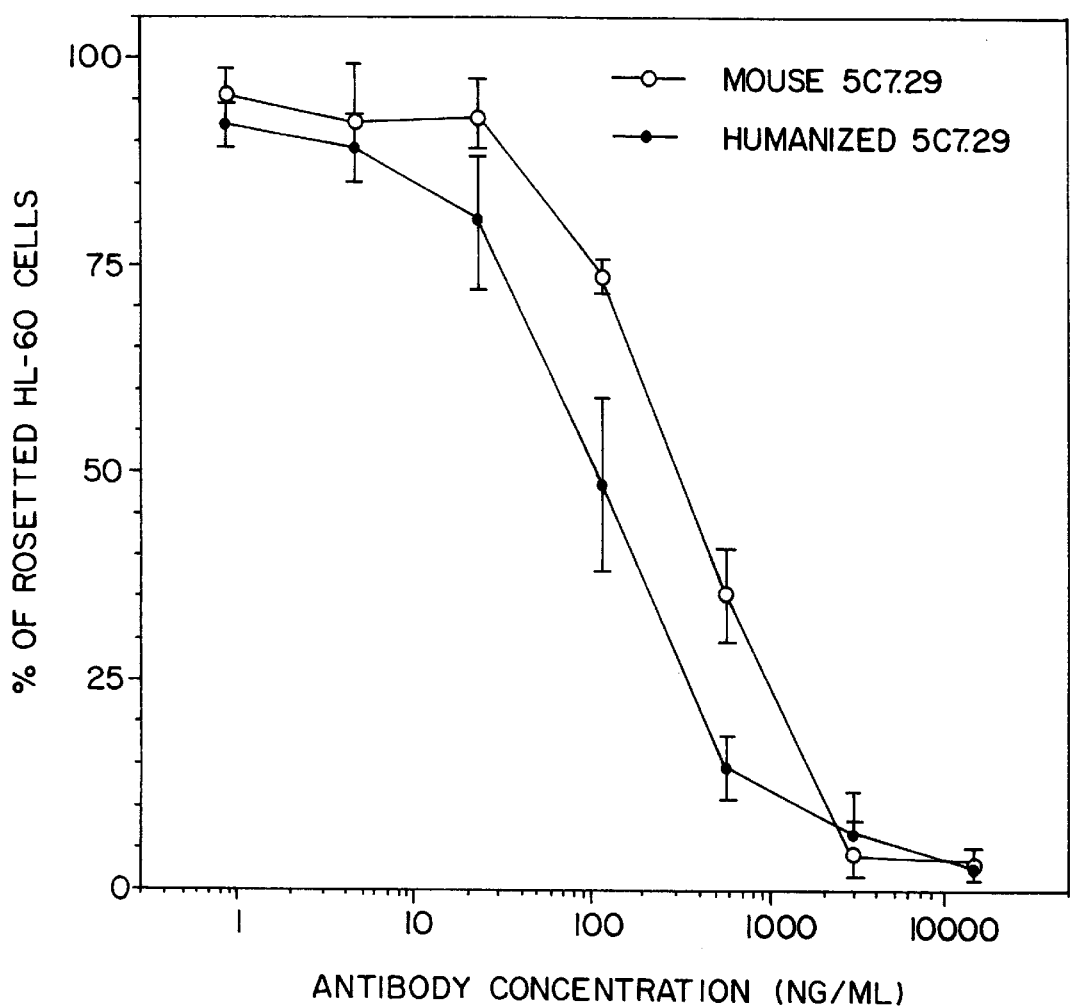
FIG. 13. Inhibition of platelet rosetting to HL-60 cells by mouse and humanized 5C7.29 antibodies. Normal human platelets were incubated with HL-60 cells in the presence of the antibodies at the indicated concentrations. After fixation, the percent of HL-60 cells with greater than 2 platelets bound (rosetted) was determined. The results shown are from a representative experiment performed with each sample in triplicate (+/−standard deviation).

To show that the humanized 5C7.29 antibody inhibits binding of P-selectin to a counter-receptor for P-selectin, its ability to inhibit the binding of HL-60 cells and activated platelets was determined. Assays of the rosetting of activated platelets to the HL-60 cells were performed as described (Berg et al., *Blood* 85:31 (1995) and supra) in the presence of monoclonal antibodies at the indicated concentrations. FIG. 13 shows that humanized 5C7.29 blocks binding of platelets to HL-60 cells as well as mouse 5C7.29. An isotype-matched control antibody had no affect on binding in this assay. The representative experiment shown was performed in triplicate and the mean and standard deviations calculated.

EXAMPLE 9

Epitoge Mapping of 5C7.29

To determine the amino acids of E-selectin involved in the binding of 5C7.29 (the epitope), the following procedure was used. DNA encoding the lectin and EGF-like domains of human E-selectin were fused to a gene encoding the human immunoglobulin lambda constant region ($C_\lambda$), which served as a tag. The chimeric DNA was inserted in a plasmid vector, which provided a lac promoter and pelB signal sequence for expression and secretion of the chimeric (fusion) protein in *E. coli*. The E-selectin domains were randomly mutagenized by error-prone polymerase chain reaction (PCR) utilizing AmpliTaq enzyme (Perkin Elmer) and $Mn^{++}$, and the amino acid substitutions were determined by DNA sequencing. *E. coli* strain TG1ΔrecA was transformed with the wild-type and mutant plasmids, and chimeric proteins were overexpressed by growing transformed *E. coli* in 2YT broth. After 8 hours of induction with 1mM IPTG, culture supernatants containing the chimeric proteins were collected. All operations were performed according to methods well-known in the art of molecular biology.

Next, 96-well plates were coated with the 5C7.29 antibody (or control antibodies). After blocking, the plates were incubated with the *E. coli* supernatants and then with HRP-conjugated anti-human $C_\lambda$ antibodies (Biosource, Camarillo, Calif.). After washing, bound enzyme was detected with TMB substrate. Supernatants containing mutant E-selectin-$C_\gamma$ chimeric protein to which 5C7.29 could still bind gave a positive signal, while supernatants containing mutant E-selectin to which 5C7.29 could not bind gave a negative signal. The results are shown in the following table, where the symbol AXB means a mutant in which the Xth amino of E-selectin form the mature N-terminus is changed from the normal A to mutant B.

TABLE 4

| Mutant | Reactivity |
|--------|------------|
| Q21R   | −          |
| R22G   | −          |
| Y23H   | −          |
| Y48H   | +          |
| E92G   | +          |
| N105S  | +          |
| K111E  | +          |
| T119A  | −          |
| A120T  | −          |

Because mutating amino acids $Q_{21}$, $R_{22}$, $Y_{23}$, $T_{119}$ and $A_{120}$ in E-selectin prevented binding of antibody 5C7.29, these amino acids must be in the epitope of 5C7.29. The full amino acid sequence of E-selectin is given in Bevilacqua, supra and in U.S. Pat. No. 5,272,263 (ELAM-1). (Another anti-E-selectin antibody was able to bind to these mutants, showing that they did not disrupt the overall structure of E-selectin). Other E/P cross-reacting antibodies that show a different pattern of reactivity with these E-selectin mutants must have a different epitope in E-selectin. The epitope of 5C7.29 in P-selectin may be determined by a similar procedure using P-selectin mutants, and may be similarly compared to the epitope of other E/P cross-reacting antibodies. The epitopes of 5C7.29 in E-selectin and P-selectin are preferred epitopes, because antibodies such as 5C7.29 that bind to them may have high affinity and blocking activity.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A recombinant monoclonal antibody comprising a first amino acid sequence from a first immunoglobulin and a second amino acid sequence from a second immunoglobulin, and having a binding site that specifically binds to P-selectin and to E-selectin, wherein the specific binding of the antibody to the P-selectin inhibits binding of the P-selectin to a counterreceptor of P-selectin; and the specific binding of the antibody to the E-selectin inhibits binding of the E-selectin to a counterreceptor of E-selectin, and wherein an excess of antibody reduces the quantity of receptor bound to counterreceptor by at least 60% as measured in an in vitro competitive binding assay.

2. The antibody of claim 1 wherein the counterreceptors are expressed on an HL-60 cell or a neutrophil.

3. The antibody of claim 1 that competes with antibody 5C7.29, ATCC accession number CRL 11640, for specific binding to P-selectin and to E-selectin.

4. The antibody of claim 1 that is a mouse antibody.

5. The antibody of claim 1 comprising a mouse variable region.

6. The antibody of claim 1 that is a human antibody.

7. The antibody of claim 1 that is a Fab, Fab', F(ab')2, Fv fragment, or a single-chain antibody.

8. The antibody of claim 1 that does not specifically bind to L-selectin.

9. The antibody of claim 1 that recognizes an epitope of E-selectin comprising amino acids Q21, R22, Y23, T119, and A120.

10. The antibody of claim 1 wherein an excess of the antibody inhibits binding to counterreceptor by at least 85% as measured in an in vitro competitive binding assay.

11. A pharmaceutical composition comprising the monoclonal antibody of claim 1.

12. A purified nucleic acid encoding a light or heavy chain variable region of the antibody of claim 1.

13. A stable cell line comprising:

a first nucleic acid encoding the heavy chain of the antibody of claim 1, the nucleic acid operably linked to a first promoter to allow expression of the heavy chain;

a second nucleic acid encoding the light chain of the antibody of claim 1, the second nucleic acid operably linked to a second promoter to allow expression of the light chain;

wherein the stable cell line can produce the antibody of claim 1.

14. A method of treating an inflammatory disease or condition, selected from adult respiratory distress syndrome and trauma, comprising administering to a human patient a therapeutically effective dose of a pharmaceutical composition comprising the antibody of claim 1.

15. A method of treating an inflammatory disease or condition selected from ischemia-reperfusion injury after myocardial infarction and stroke comprising administering to a human patient a therapeutically effective dose of a pharmaceutical composition comprising the antibody of claim 1.

16. The method of claim 15 further comprising the step of administering a therapeutically effective dose of a thrombolytic agent.

17. A humanzed antibody that specifically binds to P-selectin and inhibits the binding of the P-selectin to a counterreceptor of P-selectin; and that specifically binds to E-selectin and inhibits the binding of the E-selectin to a counterreceptor of E-selectin, said antibody comprising a humanized light chain variable region and a humanized heavy chain variable region wherein the humanized light chain variable region comprises the sequence:

DIQMTQSPSS LSASVGDRVT ITCSASSSVP YMHW-YQQKPG

KAPKLLIYDT SNLASGVPSR FSGSGSGTSY TLTISSLQPE

DFATYYCQQW SSDPFTFGQG TKVEIK (SEQ ID NO:6)

and the humanized heavy chain variable region comprises the sequence:

EVQLVESGGG LVQPGGSLRL SCAASGFTFS SFGM-HWVRQA

PGKGLEWVAF ISSGSSTIYY ADTVRGRFTI SRDN-SKNTLY

LQMNSLRAED TAVYYCARPL PPFAYWGQGT LVTVSA (SEQ ID NO:8).

18. The humanized antibody of claim 17 further comprising human light chain and heavy chain constant regions.

19. The humanized antibody of claim 17 wherein an excess of the antibody inhibits binding to counterreceptor by at least 85% as measured in an in vitro competitive binding assay.

20. A pharmaceutical composition comprising the monoclonal antibody of claim 17.

21. A purified nucleic acid encoding a light or heavy chain variable region of the antibody of claim 17.

22. The purified nucleic acid of claim 21 further encoding a human light chain or heavy chain constant region.

23. A stable cell line comprising:
    a first nucleic acid encoding the heavy chain of the antibody of claim 17, the nucleic acid operably linked to a first promoter to allow expression of the heavy chain;
    a second nucleic acid encoding the light chain of the antibody of claim 17, the second nucleic acid operably linked to a second promoter to allow expression of the light chain;
    wherein the stable cell line can produce the antibody of claim 17.

24. A method of treating an inflammatory disease or condition, selected from adult respiratory distress syndrome and trauma, comprising administering to a human patient a therapeutically effective dose of a pharmaceutical composition comprising the antibody of claim 17.

25. A method of treating an inflammatory disease or condition selected from ischemia-reperfusion injury after myocardial infarction and stroke comprising administerng to a human patient a therapeutically effective dose of a pharmaceutical composition comprising the antibody of claim 17.

26. The method of claim 25 further comprising the step of administering a therapeutically effective dose of a thrombolytic agent.

27. A humanized antibody that specifically binds to P-selectin and inhibits the binding of the P-selectin to a counterreceptor of P-selectin, and that specifically binds to E-selectin and inhibits the binding of the E-selecting to a counterrecepctor of E-selectin, said antibody comprising a humanized light chain variable region and a humanized heavy chain variable region wherein
    (1) the humanized light chain variable region comprises the sequence: $X_1IX_2X_3$TQSPSS LSASVGDRVT ITCSASSSX$_{11}$P YX$_{12}$HWYQQKPG KAPKLLIYDT SNX$_{13}$X$_{14}$X$_{15}$GVPX$_4$R X$_7$SGSGSGTX$_5$X$_6$ TX$_8$TISSLQPE DX$_9$ATYYCX$_{16}$X$_{17}$W SSDPFTFGX$_{10}$G TKVEIK (SEQ ID NO:9), wherein $X_1$=D or Q; $X_2$=Q or V; $X_3$=M or L; $X_4$=S or A; $X_5$=S or D; $X_6$=Y or F; $X_7$=F or I; $X_8$=L or F; $X_9$=F, I or A; $X_{10}$=Q, G or S; $X_{11}$=V, I or L; $X_{12}$=M or L; $X_{13}$=any amino acid; $X_{14}$=any amino acid; $X_{15}$=S or T; $X_{16}$=Q, N or H; and $X_{17}$=Q, N or H; and
    (2) the humanized heavy chain variable region comprises the sequence: $X_3$VQLVESGGG LVQPGGSLRL SCAASGFTFS SFGX$_7$HWVRQA PGKGLEWVX$_1$F ISSGSSTIYY X$_8$X$_9$X$_{10}$X$_{11}$X$_{12}$X$_{13}$RFTI SRDNX$_4$KNX$_5$LY LQMX$_2$SLRAED TAVYYCARPL PPFAYWGQGT LVTVSX$_6$ (SEQ ID NO:10); wherein, $X_1$=A or S; $X_2$=N or T; $X_3$=E, Q or D; $X_4$=S, A or P; $X_5$=T or S; $X_6$=A or S; $X_7$=M, I, V or L; $X_8$=any amino acid; $X_9$=any amino acid; $X_{10}$=amino acid; $X_{11}$=V, A, I, L, M or F; $X_{12}$=R, K or Q; and $X_{13}$=G, A, D, T or S.

28. The humanized antibody of claim 27 where in the humanized light chain variable region, $X_{11}$=V; $X_{12}$=M; $X_{13}$=L; $X_{14}$=A; $X_{15}$=S; $X_{16}$=Q; and $X_{17}$=Q; and wherein in the humanized heavy chain variables region, $X_7$=M; $X_8$=A; $X_9$=D; $X_{10}$=T; $X_{11}$=V; $X_{12}$=R; and $X_{13}$=G.

29. A pharmaceutical composition comprising the monoclonal antibody of claim 27.

30. A purified nucleic acid encoding a light or heavy chain variable region of the antibody of claim 27.

31. A stable cell line comprising;
    a first nucleic acid encoding the heavy chain of the antibody of claim 27, the nucleic acid operably linked to a first promoter to allow expression of the heavy chain;
    a second nucleic acid encoding the light chain of the antibody of claim 27, the second nucleic acid operably linked to a second promoter to allow expression of the light chain;
    wherein the stabe cell line can produce the antibody of claim 27.

32. A metod of treating an inflammatory disease or condition, selected from adult respiratory distress syndrome and trauma, comprising administering to a human patient a therapeutically effective dose of a pharmaceutical composition comprising the antibody of claim 27.

33. A method of treating an inflammatory disease or condition selected from ischemia-reperfusion injury after myocardial infarction and stroke comprising administering to a human patient a therapeutically effective dose of a pharmaceutical composition comprising the antibody of claim 27.

34. The method of claim 33 further comprising the step of administering a therapeutically effective dose of a thrombolytic agent.

35. A method of generating an antibody capable of blocking E-selectin and P-selectin mediated cell adhesion, the method comprising:
    immunizing a mammal with P-selectin;
    immunizing the mammal with E-selectin;
    immortalizing B-cells from the mammal to obtain immortalized cells producing antibodies; and
    selecting an immortalized cell producing an antibody that specifically binds to E-selectin and to P-selectin, and inhibits binding of E-selectin to a counterreceptor of E-selectin and inhibits binding P-selectin to a counter-receptor of P-selectin.

36. A monoclonal antibody that specifically binds to E-selectin and P-selectin, said antibody binding to the same epitope of E-selectin as antibody 5C7.29, ATCC accession number CRL 11640.

37. The monoclonal antibody of claim 36, said antibody further binding to the same epitope of P-selectin as antibody 5C7.29, ATCC accession number CRL 11640.

38. A humanized antibody that specifically binds to P-selectin and inhibits the binding of the P-selectin to a counterreceptor of P-selectin; and that specifically binds to E-selectin and inhibits the binding of the E-selectin to a counterreceptor of E-selectin, said antibody comprising a humanized light chain variable region and a humanized heavy chain variable region wherein
    (1) the humanized light chain variable region comprises a sequence having at least 80% sequence identity to the sequence:

DIQMTQSPSS LSASVGDRVT ITCSASSSVP YMH-WYQQKPG
KAPKLLIYDT SNLASGVPSR FSGSGSGTSY TLTISSLQPE
DFATYYCQQW SSDPFTFGQG TKVEIK (SEQ ID NO:6); and (2) the humanized heavy chain variable region comprises a sequence having at least 80% sequence identity to the sequence:

EVQLVESGGG LVQPGGSLRL SCAASGFTFS SFG-MHWVRQA
PGKGLEWVAF ISSGSSTIYY ADTVRGRFTI SRDNSKNTLY
LQMNSLRAED TAVYYCARPL PPFAYWGQGT LVTVSA (SEQ ID NO:8), wherein an excess of antibody reduces the quantity of receptor bound to counterreceptor by at least 60% as measured in an in vitro competitive binding assay.

39. The antibody of claim 38 wheren the sequence identity is at least 90%.

40. The antibody of claim 38 wherein the sequence identity is at least 95%.

41. The antibody of claim 38 wherein the counterreceptors are expressed on an HL-60 cell or a neutrophil.

42. The antibody of claim 38 that competes with antibody 5C7.29, ATCC accession number CRL 11640, for specific binding to P-selectin and to E-selectin.

43. The antibody of claim 38 that is a mouse antibody.

44. The antibody of claim 38 comprising a mouse variable region.

45. The antibody of claim 38 that is a human antibody.

46. The antibody of claim 38 that is a Fab, Fab', F(ab')2, Fv fragment or a single-chain antibody.

47. The antibody of claim 38 that does not specifically bind to L-selectin.

48. The antibody of claim 38 that recognizes an epitope of E-selectin comprising amio acids Q21, R22, Y23, T119, and A120.

49. The antibody of claim 38 wherein an excess of the antibody inhibits binding to counterreceptor by at least 85% as measured in an in vitro competitive binding assay.

50. A pharmaceutical composition comprising the monoclonal antibody of claim 38.

51. A purified nucleic acid segment encoding a light or heavy chain variable region of the antibody of claim 38.

52. A stable cell line comprising:
a nucleic acid segment encoding the heavy chain of the antibody of claim 38, the segment operably linked to a first promoter to allow expression of the heavy chain;
a second nucleic acid segment encoding the light chain of the antibody of claim 38, the second segment operably linked to a second promoter to allow expression of the light chain;
wherein the stable cell line can produce the antibody of claim 38.

53. A method of treating an inflammatory disease or condition, selected from adult respiratory distress syndrome and trauma, comprising ministering to a human patient a therapeutically effective dose of a pharmaceutical composition comprising the antibody of claim 38.

54. A method of treating an inflammatory disease or condition selected from ischemia-reperfusion injury after myocardial infarction and stoke comprising administering to a human patient a therapeutically effective dose of a pharmaceutical composition comprising the antibody of claim 38.

55. The method of claim 54 further comprising the step of administering a therapeutically effective dose of a thrombolytic agent.

* * * * *

UNITED STATES PATENT AND TRADEMARK OFFICE
CERTIFICATE OF CORRECTION

PATENT NO. : 6,210,670 B1
DATED : April 3, 2001
INVENTOR(S) : Berg, Ellen L.

It is certified that error appears in the above-identified patent and that said Letters Patent is hereby corrected as shown below:

Claim 20,
Delete "monoclonal".

Claim 25,
Replace "administerng" with "administering".

Claim 27,
Line 3, replace "P-selectin," with "P-selectin;".

Claim 28,
Line 1, replace "where in" with "wherein".

Claim 29,
Delete "monoclonal".

Claim 31,
Line 10, replace "stabe" with "stable".

Claim 32,
Replace "metod" with "method".

Claim 39,
Replace "wheren" with -- "wherein".

Claim 50,
Delete "monoclonal".

UNITED STATES PATENT AND TRADEMARK OFFICE
CERTIFICATE OF CORRECTION

PATENT NO. : 6,210,670 B1
DATED : April 3, 2001
INVENTOR(S) : Berg, Ellen L.

It is certified that error appears in the above-identified patent and that said Letters Patent is hereby corrected as shown below:

Claim 53,
Replace "ministering" with "adminstering".

Claim 54,
Replace "stoke" with stroke".

Signed and Sealed this

Twenty-third Day of October, 2001

Attest:

*Nicholas P. Godici*

Attesting Officer

NICHOLAS P. GODICI
*Acting Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 384 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..384
      (D) OTHER INFORMATION: /note= "mouse 5C7.29 antibody light
         chain variable region cDNA"

(xi) SEQUENCE DESCRIPTION: SEQ ID NO:1:

```
ATG GAT TTT CAA GTG CAG ATT TTC AGC TTC CTG CTA ATC AGT GCC TCA        48
Met Asp Phe Gln Val Gln Ile Phe Ser Phe Leu Leu Ile Ser Ala Ser
  1               5                  10                  15

GTC ATA ATA TCC AGA GGA CAA ATT GTT CTC ACC CAG TCT CCA GCA ATC        96
Val Ile Ile Ser Arg Gly Gln Ile Val Leu Thr Gln Ser Pro Ala Ile
             20                  25                  30

ATG TCT GCA TCT CCA GGG GAG AAG GTC ACC ATG ACC TGC AGT GCC AGC       144
Met Ser Ala Ser Pro Gly Glu Lys Val Thr Met Thr Cys Ser Ala Ser
         35                  40                  45
```

```
TCA AGT GTG CCT TAC ATG CAC TGG TAT CAG CAG AAG TCA GGC ACC TCC      192
Ser Ser Val Pro Tyr Met His Trp Tyr Gln Gln Lys Ser Gly Thr Ser
     50                  55                  60

CCC AAA TTA TGG ATT TAT GAC ACA TCC AAT CTG GCT TCT GGA GTC CCT      240
Pro Lys Leu Trp Ile Tyr Asp Thr Ser Asn Leu Ala Ser Gly Val Pro
65                  70                  75                  80

GCT CGC TTC AGT GGC AGT GGG TCT GGG ACC TCT TAC TCT CTC ACA ATC      288
Ala Arg Phe Ser Gly Ser Gly Ser Gly Thr Ser Tyr Ser Leu Thr Ile
                85                  90                  95

AGC AGC ATG GAG GCT GAA GAT GCT GCC ACT TAT TAC TGC CAG CAG TGG      336
Ser Ser Met Glu Ala Glu Asp Ala Ala Thr Tyr Tyr Cys Gln Gln Trp
            100                 105                 110

AGT AGT GAC CCA TTC ACG TTC GGC TCG GGG ACA AAG TTG GAA ATA AAG      384
Ser Ser Asp Pro Phe Thr Phe Gly Ser Gly Thr Lys Leu Glu Ile Lys
        115                 120                 125
```

(2) INFORMATION FOR SEQ ID NO:2:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Phe Gln Val Gln Ile Phe Ser Phe Leu Leu Ile Ser Ala Ser
1                   5                   10                  15

Val Ile Ile Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Ser Val Pro Tyr Met His Trp Tyr Gln Gln Lys Ser Gly Thr Ser
        50                  55                  60

Pro Lys Leu Trp Ile Tyr Asp Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asp Pro Phe Thr Phe Gly Ser Gly Thr Lys Leu Glu Ile Lys
        115                 120                 125
```

(2) INFORMATION FOR SEQ ID NO:3:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..405
        (D) OTHER INFORMATION: /note= "mouse 5C7.29 antibody heavy
            chain variable region cDNA"

(xi) SEQUENCE DESCRIPTION: SEQ ID NO:3:

```
ATG GAC TCC AGG CTC AAT TTA GTT TTC CTT GTC CTT ATT TTA AAA GGT       48
Met Asp Ser Arg Leu Asn Leu Val Phe Leu Val Leu Ile Leu Lys Gly
1                   5                   10                  15
```

```
GTC CAG TGT GAT GTA CGA CTG GTG GAG TCT GGG GGA GGT TTA GTG CAG      96
Val Gln Cys Asp Val Arg Leu Val Glu Ser Gly Gly Gly Leu Val Gln
         20                  25                  30

CCT GGA GGG TCC CGG AAA CTC TCC TGT GCA GCC TCT GGA TTC ACT TTC     144
Pro Gly Gly Ser Arg Lys Leu Ser Cys Ala Ala Ser Gly Phe Thr Phe
         35                  40                  45

AGT AGC TTT GGA ATG CAC TGG GTT CGT CAG GCT CCT GAT AAG GGG CTG     192
Ser Ser Phe Gly Met His Trp Val Arg Gln Ala Pro Asp Lys Gly Leu
         50                  55                  60

GAG TGG GTC GCA TTC ATT AGC AGT GGC AGT AGT ACC ATC TAC TAT GCT     240
Glu Trp Val Ala Phe Ile Ser Ser Gly Ser Ser Thr Ile Tyr Tyr Ala
 65              70                  75                      80

GAC ACA GTG AGG GGC CGA TTC ACC ATC TCC AGA GAC AGT CCC AAG AAC     288
Asp Thr Val Arg Gly Arg Phe Thr Ile Ser Arg Asp Ser Pro Lys Asn
                 85                  90                  95

ACC CTG TTC CTG CAA ATG ACC AGT CTA AGG TCT GAG GAC ACG GCC ATG     336
Thr Leu Phe Leu Gln Met Thr Ser Leu Arg Ser Glu Asp Thr Ala Met
                100                 105                 110

TAT TAC TGT GCA AGA CCT TTA CCC CCG TTT GCT TAC TGG GGC CAA GGG     384
Tyr Tyr Cys Ala Arg Pro Leu Pro Pro Phe Ala Tyr Trp Gly Gln Gly
            115                 120                 125

ACT TTG GTC ACT GTC TCT GCA                                         405
Thr Leu Val Thr Val Ser Ala
        130                 135

(2) INFORMATION FOR SEQ ID NO:4:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Ser Arg Leu Asn Leu Val Phe Leu Val Leu Ile Leu Lys Gly
 1               5                  10                  15

Val Gln Cys Asp Val Arg Leu Val Glu Ser Gly Gly Gly Leu Val Gln
             20                  25                  30

Pro Gly Gly Ser Arg Lys Leu Ser Cys Ala Ala Ser Gly Phe Thr Phe
         35                  40                  45

Ser Ser Phe Gly Met His Trp Val Arg Gln Ala Pro Asp Lys Gly Leu
     50                  55                  60

Glu Trp Val Ala Phe Ile Ser Ser Gly Ser Ser Thr Ile Tyr Tyr Ala
 65              70                  75                      80

Asp Thr Val Arg Gly Arg Phe Thr Ile Ser Arg Asp Ser Pro Lys Asn
                 85                  90                  95

Thr Leu Phe Leu Gln Met Thr Ser Leu Arg Ser Glu Asp Thr Ala Met
                100                 105                 110

Tyr Tyr Cys Ala Arg Pro Leu Pro Pro Phe Ala Tyr Trp Gly Gln Gly
            115                 120                 125

Thr Leu Val Thr Val Ser Ala
        130                 135

(2) INFORMATION FOR SEQ ID NO:5:

(i) SEQUENCE CHARACTERISTICS:
        (A) LENGTH: 384 base pairs
        (B) TYPE: nucleic acid
        (C) STRANDEDNESS: single
        (D) TOPOLOGY: linear
```

(ii) MOLECULE TYPE: DNA (ix) FEATURE:
    (A) NAME/KEY: CDS
    (B) LOCATION: 1..384
    (D) OTHER INFORMATION: /note= "humanized 5C7.29 antibody light
        chain variable region synthetic DNA"

(xi) SEQUENCE DESCRIPTION: SEQ ID NO:5:

```
ATG GAT TTT CAA GTG CAG ATT TTC AGC TTC CTG CTA ATC AGT GCC TCA      48
Met Asp Phe Gln Val Gln Ile Phe Ser Phe Leu Leu Ile Ser Ala Ser
 1               5                  10                  15

GTC ATA ATA TCC AGA GGA GAT ATT CAA ATG ACC CAG TCT CCA TCT AGC      96
Val Ile Ile Ser Arg Gly Asp Ile Gln Met Thr Gln Ser Pro Ser Ser
             20                  25                  30

TTA TCT GCA TCT GTA GGG GAT AGG GTC ACC ATA ACC TGC AGT GCC AGC     144
Leu Ser Ala Ser Val Gly Asp Arg Val Thr Ile Thr Cys Ser Ala Ser
         35                  40                  45

TCA AGT GTG CCT TAC ATG CAC TGG TAT CAG CAG AAG CCA GGC AAA GCC     192
Ser Ser Val Pro Tyr Met His Trp Tyr Gln Gln Lys Pro Gly Lys Ala
     50                  55                  60

CCC AAA TTA TTG ATT TAT GAC ACA TCC AAT CTG GCT TCT GGA GTC CCT     240
Pro Lys Leu Leu Ile Tyr Asp Thr Ser Asn Leu Ala Ser Gly Val Pro
 65                  70                  75                  80

TCT CGC TTC AGT GGC AGT GGG TCT GGG ACC TCT TAC ACT CTC ACA ATC     288
Ser Arg Phe Ser Gly Ser Gly Ser Gly Thr Ser Tyr Thr Leu Thr Ile
                 85                  90                  95

AGC AGC CTG CAG CCT GAA GAT TTT GCC ACT TAT TAC TGC CAG CAG TGG     336
Ser Ser Leu Gln Pro Glu Asp Phe Ala Thr Tyr Tyr Cys Gln Gln Trp
            100                 105                 110

AGT AGT GAC CCA TTC ACG TTC GGC CAG GGG ACA AAG GTG GAA ATA AAG     384
Ser Ser Asp Pro Phe Thr Phe Gly Gln Gly Thr Lys Val Glu Ile Lys
        115                 120                 125
```

(2) INFORMATION FOR SEQ ID NO:6:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asp Phe Gln Val Gln Ile Phe Ser Phe Leu Leu Ile Ser Ala Ser
 1               5                  10                  15

Val Ile Ile Ser Arg Gly Asp Ile Gln Met Thr Gln Ser Pro Ser Ser
             20                  25                  30

Leu Ser Ala Ser Val Gly Asp Arg Val Thr Ile Thr Cys Ser Ala Ser
         35                  40                  45

Ser Ser Val Pro Tyr Met His Trp Tyr Gln Gln Lys Pro Gly Lys Ala
     50                  55                  60

Pro Lys Leu Leu Ile Tyr Asp Thr Ser Asn Leu Ala Ser Gly Val Pro
 65                  70                  75                  80

Ser Arg Phe Ser Gly Ser Gly Ser Gly Thr Ser Tyr Thr Leu Thr Ile
                 85                  90                  95

Ser Ser Leu Gln Pro Glu Asp Phe Ala Thr Tyr Tyr Cys Gln Gln Trp
            100                 105                 110

Ser Ser Asp Pro Phe Thr Phe Gly Gln Gly Thr Lys Val Glu Ile Lys
        115                 120                 125
```

(2) INFORMATION FOR SEQ ID NO:7:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..405
        (D) OTHER INFORMATION: /note= "humanized 5C7.29 antibody heavy
            chain variable region synthetic DNA"

(xi) SEQUENCE DESCRIPTION: SEQ ID NO:7:

```
ATG GAC TCC AGG CTC AAT TTA GTT TTC CTT GTC CTT ATT TTA AAA GGT        48
Met Asp Ser Arg Leu Asn Leu Val Phe Leu Val Leu Ile Leu Lys Gly
 1               5                  10                  15

GTC CAG TGT GAA GTA CAA CTG GTG GAG TCT GGG GGA GGT TTA GTG CAG        96
Val Gln Cys Glu Val Gln Leu Val Glu Ser Gly Gly Gly Leu Val Gln
             20                  25                  30

CCT GGA GGG TCC CTT CGT CTC TCC TGT GCA GCC TCT GGA TTC ACT TTC       144
Pro Gly Gly Ser Leu Arg Leu Ser Cys Ala Ala Ser Gly Phe Thr Phe
         35                  40                  45

AGT AGC TTT GGA ATG CAC TGG GTT CGT CAG GCT CCT GGT AAG GGG CTG       192
Ser Ser Phe Gly Met His Trp Val Arg Gln Ala Pro Gly Lys Gly Leu
     50                  55                  60

GAG TGG GTC GCA TTC ATT AGC AGT GGC AGT AGT ACC ATC TAC TAT GCT       240
Glu Trp Val Ala Phe Ile Ser Ser Gly Ser Ser Thr Ile Tyr Tyr Ala
 65                  70                  75                  80

GAC ACA GTG AGG GGC CGA TTC ACC ATC TCC AGA GAC AAC ACC AAG AAC       288
Asp Thr Val Arg Gly Arg Phe Thr Ile Ser Arg Asp Asn Thr Lys Asn
                 85                  90                  95

ACC CTG TAT CTG CAA ATG AAC AGT CTA AGG GCT GAG GAC ACG GCC GTG       336
Thr Leu Tyr Leu Gln Met Asn Ser Leu Arg Ala Glu Asp Thr Ala Val
             100                 105                 110

TAT TAC TGT GCA AGA CCT TTA CCC CCG TTT GCT TAC TGG GGC CAA GGG       384
Tyr Tyr Cys Ala Arg Pro Leu Pro Pro Phe Ala Tyr Trp Gly Gln Gly
         115                 120                 125

ACT TTG GTC ACT GTC TCT GCA                                           405
Thr Leu Val Thr Val Ser Ala
     130                 135
```

(2) INFORMATION FOR SEQ ID NO:8:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asp Ser Arg Leu Asn Leu Val Phe Leu Val Leu Ile Leu Lys Gly
 1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Phe Gly Met His Trp Val Arg Gln Ala Pro Gly Lys Gly Leu
     50                  55                  60
```

```
Glu Trp Val Ala Phe Ile Ser Ser Gly Ser Ser Thr Ile Tyr Tyr Ala
 65                  70                  75                  80

Asp Thr Val Arg Gly Arg Phe Thr Ile Ser Arg Asp Asn Thr Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Pro Leu Pro Pro Phe Ala Tyr Trp Gly Gln Gly
        115                 120                 125

Thr Leu Val Thr Val Ser Ala
    130             135
```

(2) INFORMATION FOR SEQ ID NO:9:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER" /note= "Xaa = Asp or Gln"

(ix) FEATURE:
        (A) NAME/KEY: Modified-site
        (B) LOCATION: 3
        (D) OTHER INFORMATION: /product= "OTHER" /note= "Xaa = Gln or Val"

(ix) FEATURE:
        (A) NAME/KEY: Modified-site
        (B) LOCATION: 4
        (D) OTHER INFORMATION: /product= "OTHER" /note= "Xaa = Met or Leu"

(ix) FEATURE:
        (A) NAME/KEY: Modified-site
        (B) LOCATION: 29
        (D) OTHER INFORMATION: /product= "OTHER" /note= "Xaa = Val, Ile or Leu"

(ix) FEATURE:
        (A) NAME/KEY: Modified-site
        (B) LOCATION: 32
        (D) OTHER INFORMATION: /product= "OTHER" /note= "Xaa = Met or Leu"

(ix) FEATURE:
        (A) NAME/KEY: Modified-site
        (B) LOCATION: 53
        (D) OTHER INFORMATION: /product= "OTHER" /note= "Xaa = any amino acid"

(ix) FEATURE:
        (A) NAME/KEY: Modified-site
        (B) LOCATION: 54
        (D) OTHER INFORMATION: /product= "OTHER" /note= "Xaa = any amino acid"

(ix) FEATURE:
        (A) NAME/KEY: Modified-site
        (B) LOCATION: 55
        (D) OTHER INFORMATION: /product= "OTHER" /note= "Xaa = Ser or Thr"

(ix) FEATURE:
        (A) NAME/KEY: Modified-site
        (B) LOCATION: 59
        (D) OTHER INFORMATION: /product= "OTHER" /note= "Xaa = Ser or Ala"

```
    (ix) FEATURE:
          (A) NAME/KEY: Modified-site
          (B) LOCATION: 61
          (D) OTHER INFORMATION: /product= "OTHER" /note= "Xaa = Phe or
              Ile"

(ix) FEATURE:
          (A) NAME/KEY: Modified-site
          (B) LOCATION: 69
          (D) OTHER INFORMATION: /product= "OTHER" /note= "Xaa = Ser or
              Asp"

(ix) FEATURE:
          (A) NAME/KEY: Modified-site
          (B) LOCATION: 70
          (D) OTHER INFORMATION: /product= "OTHER" /note= "Xaa = Tyr or
              Phe"

(ix) FEATURE:
          (A) NAME/KEY: Modified-site
          (B) LOCATION: 72
          (D) OTHER INFORMATION: /product= "OTHER" /note= "Xaa = Leu or
              Phe"

(ix) FEATURE:
          (A) NAME/KEY: Modified-site
          (B) LOCATION: 82
          (D) OTHER INFORMATION: /product= "OTHER" /note= "Xaa = Phe,
              Ile or Ala"

(ix) FEATURE:
          (A) NAME/KEY: Modified-site
          (B) LOCATION: 88
          (D) OTHER INFORMATION: /product= "OTHER" /note= "Xaa = Gln,
              Asn or His"

(ix) FEATURE:
          (A) NAME/KEY: Modified-site
          (B) LOCATION: 89
          (D) OTHER INFORMATION: /product= "OTHER" /note= "Xaa = Gln,
              Asn or His"

(ix) FEATURE:
          (A) NAME/KEY: Modified-site
          (B) LOCATION: 99
          (D) OTHER INFORMATION: /product= "OTHER" /note= "Xaa = Gln,
              Gly or Ser"

(xi) SEQUENCE DESCRIPTION: SEQ ID NO:9:

Xaa Ile Xaa Xaa Thr Gln Ser Pro Ser Ser Leu Ser Ala Ser Val Gly
 1               5                  10                  15

Asp Arg Val Thr Ile Thr Cys Ser Ala Ser Ser Xaa Pro Tyr Xaa
             20                  25                  30

His Trp Tyr Gln Gln Lys Pro Gly Lys Ala Pro Lys Leu Leu Ile Tyr
             35                  40                  45

Asp Thr Ser Asn Xaa Xaa Xaa Gly Val Pro Xaa Arg Xaa Ser Gly Ser
 50                  55                  60

Gly Ser Gly Thr Xaa Xaa Thr Xaa Thr Ile Ser Ser Leu Gln Pro Glu
 65                  70                  75                  80

Asp Xaa Ala Thr Tyr Tyr Cys Xaa Xaa Trp Ser Ser Asp Pro Phe Thr
             85                  90                  95

Phe Gly Xaa Gly Thr Lys Val Glu Ile Lys
            100                 105

(2) INFORMATION FOR SEQ ID NO:10:

(i) SEQUENCE CHARACTERISTICS:
          (A) LENGTH: 116 amino acids
          (B) TYPE: amino acid
          (C) STRANDEDNESS:
```

(D) TOPOLOGY: linear (ii) MOLECULE TYPE: peptide (ix) FEATURE:
       (A) NAME/KEY: Modified-site
       (B) LOCATION: 1
       (D) OTHER INFORMATION: /product= "OTHER" /note= "Xaa = Glu,
           Gln or Asp"

(ix) FEATURE:
       (A) NAME/KEY: Modified-site
       (B) LOCATION: 34
       (D) OTHER INFORMATION: /product= "OTHER" /note= "Xaa = Met,
           Ile, Val or Leu"

(ix) FEATURE:
       (A) NAME/KEY: Modified-site
       (B) LOCATION: 49
       (D) OTHER INFORMATION: /product= "OTHER" /note= "Xaa = Ala or
           Ser"

(ix) FEATURE:
       (A) NAME/KEY: Modified-site
       (B) LOCATION: 61
       (D) OTHER INFORMATION: /product= "OTHER" /note= "Xaa = any
           amino acid"

(ix) FEATURE:
       (A) NAME/KEY: Modified-site
       (B) LOCATION: 62
       (D) OTHER INFORMATION: /product= "OTHER" /note= "Xaa = any
           amino acid"

(ix) FEATURE:
       (A) NAME/KEY: Modified-site
       (B) LOCATION: 63
       (D) OTHER INFORMATION: /product= "OTHER" /note= "Xaa = any
           amino acid"

(ix) FEATURE:
       (A) NAME/KEY: Modified-site
       (B) LOCATION: 64
       (D) OTHER INFORMATION: /product= "OTHER" /note= "Xaa = Val,
           Ala, Ile, Leu, Met or Phe"

(ix) FEATURE:
       (A) NAME/KEY: Modified-site
       (B) LOCATION: 65
       (D) OTHER INFORMATION: /product= "OTHER" /note= "Xaa = Arg,
           Lys or Gln"

(ix) FEATURE:
       (A) NAME/KEY: Modified-site
       (B) LOCATION: 66
       (D) OTHER INFORMATION: /product= "OTHER" /note= "Xaa = Gly,
           Ala, Asp, Thr or Ser"

(ix) FEATURE:
       (A) NAME/KEY: Modified-site
       (B) LOCATION: 75
       (D) OTHER INFORMATION: /product= "OTHER" /note= "Xaa = Ser,
           Ala or Pro"

(ix) FEATURE:
       (A) NAME/KEY: Modified-site
       (B) LOCATION: 78
       (D) OTHER INFORMATION: /product= "OTHER" /note= "Xaa = Thr or
           Ser"

(ix) FEATURE:
       (A) NAME/KEY: Modified-site
       (B) LOCATION: 84
       (D) OTHER INFORMATION: /product= "OTHER" /note= "Xaa = Asn or
           Thr"

(ix) FEATURE:
       (A) NAME/KEY: Modified-site
       (B) LOCATION: 116

(D) OTHER INFORMATION: /product= "OTHER" /note= "Xaa = Ala or
                    Ser"

(xi) SEQUENCE DESCRIPTION: SEQ ID NO:10:

Xaa Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Xaa His Trp Val Arg Gln Ala Pro Gly Lys Gly Leu Glu Trp Val
        35                  40                  45

Xaa Phe Ile Ser Ser Gly Ser Ser Thr Ile Tyr Tyr Xaa Xaa Xaa Xaa
    50                  55                  60

Xaa Xaa Arg Phe Thr Ile Ser Arg Asp Asn Xaa Lys Asn Xaa Leu Tyr
65              70                  75                  80

Leu Gln Met Xaa Ser Leu Arg Ala Glu Asp Thr Ala Val Tyr Tyr Cys
            85                  90                  95

Ala Arg Pro Leu Pro Pro Phe Ala Tyr Trp Gly Gln Gly Thr Leu Val
            100                 105                 110

Thr Val Ser Xaa
            115